(12) United States Patent
Bäckström et al.

(10) Patent No.: US 6,903,114 B2
(45) Date of Patent: Jun. 7, 2005

(54) DERIVATIVES OF NAPHTHALENE WITH COMT INHIBITING ACTIVITY

(75) Inventors: Reijo Bäckström, Helsinki (FI); Jarmo Pystynen, Espoo (FI); Timo Lotta, Vantaa (FI); Martti Ovaska, Espoo (FI); Jyrki Taskinen, Helsinki (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 10/380,286

(22) PCT Filed: Sep. 14, 2001

(86) PCT No.: PCT/FI01/00797
§ 371 (c)(1),
(2), (4) Date: Jul. 9, 2003

(87) PCT Pub. No.: WO02/22551
PCT Pub. Date: Mar. 21, 2002

(65) Prior Publication Data
US 2004/0034011 A1 Feb. 19, 2004

(30) Foreign Application Priority Data
Sep. 15, 2000 (FI) .............................................. 20002044

(51) Int. Cl.$^7$ ........................ C07D 215/20; A61K 31/47
(52) U.S. Cl. ........................ 514/307; 514/311; 514/646; 514/693; 514/715; 546/139; 546/152; 564/305; 568/425; 568/633
(58) Field of Search ................................. 514/307, 311, 514/646, 693, 715; 546/139, 152; 564/305; 568/425, 633

(56) References Cited

U.S. PATENT DOCUMENTS

| 3,973,608 | A | 8/1976 | Umezawa et al. |
| 5,389,653 | A | 2/1995 | Bernauer et al. |
| 5,446,194 | A | 8/1995 | Bäckström et al. |
| 5,650,439 | A | 7/1997 | Nakamura et al. |
| 5,780,675 | A | 7/1998 | Royer et al. |
| 6,150,412 | A | 11/2000 | Pystynen et al. |

FOREIGN PATENT DOCUMENTS

| WO | WO 96/37456 | 11/1996 |
| WO | WO 98/27973 | 7/1998 |

OTHER PUBLICATIONS

Stipanovic et al, Phytochemistry, vol 19 No. 8, pp. 1735–8, 1980.*
Abraham et al, Phytochemistry, vol 52, No. 5, pp. 829–836, 1999.*
Guo et al, Chemical Abstracts, Abstract No. 108:204, 394, Jun. 11, 1988.*

Servin et al., "Metabolism of 6,7–dimethoxy 4–(4'–chlorobenzyl)isoquinoline. II. Role of liver catechol O–methyltransferase and glutathione," Xenobiotica, vol. 17, pp. 1381–1391 (1987).

Smit et al., "Catechol–O–Methyltransferase as a Target for Melanoma Destruction?," Biochemical Pharmacology, vol. 48, pp. 743–752 (1994).

Lautala et al., "Molecular Mechanisms Controlling the Rate and Specificity of Catechol O–Methylation by Human Soluble Catechol O–Methyltransferase," Molecular Pharmacology, vol. 59, pp. 393–402 (2001).

Lombardi et al., "Enzymatic Methylation of Microsomal Metabolites of Benzo(a)pyrene," Cancer Research, vol. 41, pp. 4415–4419 (1981).

Kaakkola, "Clinical Pharmacology, Therapeutic Use and Potential of COMT Inhibitors in Parkinson's Disease," Drugs, vol. 59, pp. 1233–1250 (2000).

Borchardt et al., "Catechol O–Methyltransferase. 12. Affinity Labeling the Active Site with the Oxidation Products of 5,6–Dihydroxyindole", J. Med. Chem., vol. 25, pp. 263–271 (1982).

Lotta et al., "Kinetics of Human Soluble and Membrane–Bound Catechol O–Methyltransferase: A Revised Mechanism and Description of the Thermolabile Variant of the Enzyme", Biochemistry, vol. 34, pp. 4202–4210 (1995).

Smissman et al., "Synthesis and Biological Activity of 2– and 4–Substituted 6,7–Dihydroxy–1,2,3,4–tetrahydroisoquinolines", Journal of Medicinal Chemistry, vol. 19, No. 1, pp. 127–131 (1976).

Borchardt et al., "Catechol O–Methyltransferase. 8. Structure–Activity Relationships for Inhibition by 8–Hydroxyquinolines", Journal of Medicinal Chemistry, vol. 19, No. 4, pp. 558–560 (1976).

* cited by examiner

Primary Examiner—Zinna Northington Davis
(74) Attorney, Agent, or Firm—Finnegan, Henderson, Farabow, Garrett & Dunner, LLP

(57) ABSTRACT

Compounds of formula (I'), wherein A, $R_1$ to $R_3$ and t are as defined in the disclosure, exhibit COMT enzyme inhibiting activity so that they are useful as COMT inhibitors.

16 Claims, No Drawings

DERIVATIVES OF NAPHTHALENE WITH COMT INHIBITING ACTIVITY

This application is a national stage filing of PCT International Application No. PCT/FI01/00797, filed on Sep. 14, 2001. This application also claims the benefit of priority under 35 U.S.C. §119(a) to Finnish patent application no. 20002044, filed on Sep. 15, 2000.

FIELD OF THE INVENTION

The present invention relates to derivatives of naphthalene and pharmaceutically acceptable salts and esters thereof. The invention further relates to pharmaceutical compositions thereof and to their use as inhibitors of catechol-O-methyltransferase (COMT) enzyme.

BRIEF DESCRIPTION OF THE PRIOR ART

Compounds with COMT inhibiting activity are already known. For example, derivatives of catechols have been disclosed i.a. in U.S. Pat. Nos. 5,446,194, 5,389,653 and WO-A-96 37456. U.S. Pat. Nos. 5,650,439 and 3,973,608 relate to isoflavones and, respectively, to a purpurogallin derivative with COMT inhibiting activity. Furthermore, R. T. Borchardt and P. Bhatia disclose in J. Med. Chem., vol.25, 1982, p.263–271, analogues of 5,6-dihydroxyindole (5,6-DHI) as COMT inhibitors. COMT inhibitors are used i.a. in the treatment of Parkinson's disease. COMT-inhibitors have also indicated to be useful in the treatment of i.a. hypertension, heart failure and depression (cf. e.g. U.S. Pat. No. 5,446,194 above) as well as inhibitors for the prevention of diabetic vascular dysfunctions (cf. WO-A-98 27973).

SUMMARY OF THE INVENTION

The object of the present invention is to provide further compounds with catechol-O-methyltransferase enzyme inhibiting activity.

The invention also provides compounds for the treatment of disorders or conditions wherein inhibition of COMT is indicated to be useful, as well as a use thereof for the manufacture of a medicament to be used as a COMT inhibiting agent. Furthermore, pharmaceutical compositions containing the present compounds are provided.

DETAILED DESCRIPTION OF THE INVENTION

The invention thus provides compounds of the general formula I':

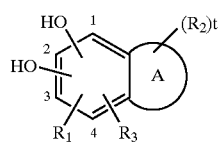

wherein the two OH— substituents in the phenyl moiety are in a position ortho to one another and R1 in a position ortho to one of the hydroxy groups; and wherein "A" is a fused ring moiety selected from benzo ring and a 6-membered heteroaromatic ring which contains one or two N heteroatoms;

$R_1$ is $NO_2$, CN, CHO, $CF_3$ or $(C_1-C_6)$alkyl-CO—;

t is 0, 1, 2, 3 or 4;

each $R_2$ is selected independently from OH, halogen, $NO_2$, SH, $NH_2$, $(C_1-C_6)$alkyl, $(C_2-C_6)$alkenyl, $(C_1-C_6)$alkoxy, OH—$(C_1-C_6)$alkyl, $NH_2$—$(C_1-C_6)$alkyl, $NH_2$—$(C_1-C_6)$alkyl, halo-$(C_1C_6)$alkyl, mono- or di$(C_1-C_6)$alkylamino, $SO_2R_4$, $(C_1-C_{20})$alkyl-CO—, halo-$(C_1-C_6)$alkyl-CO—, phenyl-N=N— optionally substituted with one to three substituents $R_6$, —$(Y)_n$—$(B)_m$—COOH and —$(Y)_n$—$(B)_m$—$R_5$;

$R_3$ is H, $NO_2$, CN, CHO, halogen, $CF_3$ or $(C_1-C_6)$alkyl; and $R_4$ is $(C_1-C_6)$alkyl, $NH_2$, OH or mono- or di$(C_1-C_6)$alkylamino;

m is 0 or 1;

n is 0 or 1;

Y is —CO— or —CHOH—;

B is $(C_1-C_6)$alkylene or $(C_2-C_6)$alkenylene;

$R_5$ is phenyl, naphthyl, $(C_3-C_7)$cycloalkyl or 5- to 10-membered heterocyclyl with one to four heteroatoms each selected independently from N, O and S, wherein the said phenyl, naphthyl, $(C_3-C_7)$cycloalkyl or 5- to 10-membered heterocyclyl is optionally substituted with one to five substituents $R_6$, or $R_5$ is

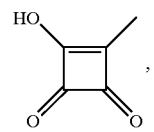

each $R_6$ is selected independently from OH, halogen, COOH, 5-tetrazolyl, $NO_2$, SH, $NH_2$, CN, CHO, =O, $(C_1-C_6)$alkyl, $(C_1-C_6)$alkoxy, halo-$(C_1-C_6)$alkyl, mono- or di$(C_1-C_6)$alkylamino, CO—$(C_1-C_6)$alkyl, CO—$NH_2$, mono- or di$(C_1-C_6)$alkylamino-CO—, NHOH, CONHOH or $SO_2R_4$;

or pharmaceutically acceptable salts or esters thereof.

As a subgroup of the compounds I' the invention provides new compounds of formula I,

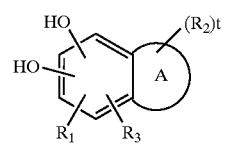

wherein the two OH— substituents in the phenyl moiety are in a position ortho to one another and $R_1$ in a position ortho to one of the hydroxy groups; and wherein A and $R_2$ are as defined above;

t is 1, 2, 3 or 4;

$R_1$ is $NO_2$, CN, CHO or $CF_3$; and $R_3$ is H, $NO_2$, CN, CHO, halogen, $CF_3$ or $CH_3$;

or pharmaceutically acceptable salts or pharmaceutically acceptable esters thereof.

The compounds of formula I' and I exhibit COMT inhibiting activity and can thus be used as therapeuticals for the treatment of diseases or conditions wherein COMT inhibitors are indicated to be useful, e.g. for the treatment of Parkinson's disease.

The two OH-substitutents in the compounds of formulae I' and/or I can be in the 1,2-positions, 2,3-positions or 3,4-positions, and preferably in the 2,3-positions, according to the numbering of the above formula I'.

The following subgroups (1) to (23) of compounds of formula I' or I taken alone or in any combination with each other are preferable, (1) $R_1$ is $NO_2$, CN, CHO or $CF_3$, e.g. $NO_2$, CN or CHO, such as $NO_2$ or CN, e.g. $NO_2$;

(2) t is 1, 2 or 3, e.g. 1 or 2, such as 1; or in the compounds I' t is 0, 1 or 2;

(3) $R_3$ is H, methyl, halogen, $NO_2$ or CHO, such as H or halogen, e.g. H;

(4) A is a fused benzene ring;

(5) A is a fused 6-membered heteroaromatic ring which contains 1 or 2, e.g. 1, heteroatoms selected from N;

(6) each $R_2$ is selected independently from OH, halogen, $NO_2$, $NH_2$, $(C_1-C_6)$alkyl, $(C_2-C_6)$alkenyl, $(C_1-C_6)$alkoxy, OH—$(C_{1-6})$alkyl, $NH_2$—$(C_1-C_6)$alkyl, halo-$(C_1-C_6)$alkyl, mono- or di$(C_1-C_6)$alkylamino, $SO_2R_4$ (wherein $R_4$ is $(C_1-C_6)$alkyl, OH, $NH_2$ or mono- or di$(C_1-C_6)$alkylamino, e.g. OH, $NH_2$ or mono- or di$(C_1-C_6)$alkylamino, such as mono- or di$(C_1-C_6)$alkylamino), $(C_1-C_{20})$alkyl-CO—, e.g. $(C_1-C_9)$alkyl-CO—, such as $(C_1-C_6)$alkyl-CO—halo-$(C_1-C_6)$alkyl-CO—, phenyl-N=N— (unsubstituted or substituted with one to three, e.g. one or two, e.g. one, substituent(s) $R_6$), —$(Y)_n$—$(B)_m$—COOH (e.g. —$(B)_m$—COOH and —Y—B—COOH) and —$(Y)_n$—$(B)_m$—$R_5$; wherein n is 0 or 1; m is 0 or 1; Y is —CO— or —CHOH—, e.g. —CO—; B is $(C_1-C_6)$alkylene or $(C_2-C_6)$alkenylene, e.g. $(C_1-C_6)$alkylene; $R_5$ is phenyl, naphthyl, $(C_3-C_7)$cycloalkyl or 5- to 10-membered, e.g. 5- or 6-membered, heterocyclyl with one to four heteroatoms each selected independently from N, O and S, e.g. phenyl, $(C_3-C_7)$cycloalkyl or 5- to 10-membered heterocyclic ring with one to four heteroatoms each selected independently from N, O and S (e.g. piperidyl, piperazinyl, morpholinyl, tetrazolyl, pyrrolyl, pyrrolinyl, pyrrolidinyl, thienyl, furyl, oxadiazolyl, isoindolinyl, pyridazinyl or pyridyl, e.g. tetrazolyl, piperidinyl, morpholinyl, piperazinyl, pyrrolyl, pyrrolidinyl, pyrrolinyl or pyridyl, such as tetrazolyl, piperazinyl, pyrrolyl or pyrrolinyl, e.g. piperazinyl, pyrrolyl or pyrrolinyl) each of which is optionally substituted with one to five, e.g. one to three, such as one or two, e.g. one, substituent(s) $R_6$ as defined above or below; or $R_5$ is

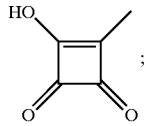
;

(7) each $R_2$ is selected independently from $NO_2$, $NH_2$, OH, $SO_2R_4$ (wherein $R_4$ is OH, $NH_2$ or mono- or di$(C_1-C_6)$alkylamino, e.g. mono- or di$(C_1-C_6)$alkylamino), $(C_1-C_6)$alkyl, $NH_2$—$(C_1-C_6)$alkyl, $(C_1-C_9)$alkyl-CO—, halo-$(C_1-C_6)$alkyl-CO—, phenyl-N=N— (wherein the phenyl moiety is unsubstituted or substituted with one to three, e.g. one or two, e.g. one, substituent(s) $R_6$), —$(Y)_n$—$(B)_m$—COOH (e.g. —$(B)_m$—COOH and —Y—B—COOH) and —$(Y)_n$—$(B)_m$—$R_5$; wherein n is 0; or n is 1 and Y is —CO— or —CHOH—, e.g. —CO—; m is 0; or m is 1 and B is $(C_1-C_6)$alkylene or $(C_2-C_6)$alkenylene, e.g. $(C_1-C_6)$alkylene; $R_5$ is phenyl, naphthyl,$(C_3-C_7)$cycloalkyl or 5- to 10-membered, e.g. 5- or 6-membered, heterocyclic ring with one to four heteroatoms each selected independently from N, O and S, e.g. phenyl, $(C_3-C_7)$cycloalkyl or 5- to 10-membered heterocyclic ring with one to four heteroatoms each selected independently from N, O and S (e.g. piperidyl, piperazinyl, morpholinyl, tetrazolyl, pyrrolyl, pyrrolinyl, pyrrolidinyl, thienyl, furyl, oxadiazolyl, isoindolinyl, pyridazinyl or pyridyl, e.g. tetrazolyl, piperidinyl, morpholinyl, piperazinyl, pyrrolyl, pyrrolidinyl, pyrrolinyl or pyridyl, such as tetrazolyl, piperazinyl, pyrrolyl or pyrrolinyl, e.g. piperazinyl, pyrrolyl or pyrrolinyl) each of which is unsubstituted or substituted with one to five, e.g. one to three, such as one or two, substituent(s) $R_6$ as defined above or below;

(8) $R_2$ is selected independently from $SO_2R_4$ (wherein $R_4$ is OH, $NH_2$ or mono- or di$(C_1-C_6)$alkylamino), phenyl-N=N— (unsubstituted or substituted with one to three, e.g. one or two, e.g. one, substituents $R_6$), —$(Y)_n$—$(B)_m$—COOH and —$(Y)_n$—$(B)_m$—$R_5$; wherein n is 0; or n is 1 and Y is —CO— or —CHOH—, e.g. —CO—; m is 0; or m is 1 and B is $(C_1-C_6)$alkylene or $(C_2-C_6)$alkenylene, e.g. $(C_1-C_6)$alkylene; and $R_5$ is as defined above or below; e.g. $R_2$ is $SO_2R_4$ (wherein $R_4$ is as defined above or below), phenyl-N=N— (wherein the phenyl moiety is unsubstituted or substituted with one to three, e.g. one or two, e.g. one, substituent(s) $R_6$), —$(Y)_n$—$(B)_m$—COOH and —$(Y)_n$—$(B)_m$—$R_5$;

(9) $R_2$ is selected independently from $NO_2$, $NH_2$, OH, $SO_2R_4$ (wherein $R_4$ is OH, $NH_2$ or mono- or di$(C_1-C_6)$alkylamino, e.g. mono- or di$(C_1-C_6)$alkylamino), $(C_1-C_6)$alkyl, $(C_1-C_6)$alkoxy, $NH_2$—$(C_1-C_6)$alkyl, $(C_1-C_9)$alkyl-CO—, halo-$(C_1-C_6)$alkyl-CO—, phenyl-N=N— (wherein the phenyl moiety is unsubstituted or substituted with one to three, e.g. one or two, e.g. one, substituent(s) $R_6$) and —$(Y)_n$—$(B)_m$—$R_5$; wherein n is 0; or n is 1 and Y is —CO— or —CHOH—, e.g. —CO—; m is 0; or m is 1 and B is $(C_1-C_6)$alkylene or $(C_2-C_6)$alkenylene, e.g. $(C_1-C_6)$alkylene; e.g. $R_2$ is selected from $(C_1-C_6)$alkyl, $NH_2$—$(C_1-C_6)$alkyl, $(C_1-C_9)$alkyl-CO—, halo-$(C_1C_6)$alkyl-CO—, phenyl-N=N— (wherein the phenyl moiety is unsubstituted or substituted with one to three, e.g. one or two, e.g. one, substituent(s) $R_6$) and —$(Y)_n$—$(B)_m$—$R_5$, wherein Y, B n, m and $R_5$ are as defined above or below;

(10) t is 1 or 2 and $R_2$ or, resp., one of $R_2$ is as defined in point (8) or (9) above;

(11) t is 2 or 3, e.g. 2, and one of $R_2$ is as defined in point (8) and the other $R_2$ is/are selected independently from OH, halogen, $NO_2$, $NH_2$, $(C_1-C_6)$alkyl, $(C_2-C_6)$alkenyl, $(C_1-C_6)$alkoxy, OH—$(C_1-C_6)$alkyl, halo-$(C_1-C_6)$alkyl, $NH_2$—$(C_1-C_6)$alkyl, $(C_1-C_9)$alkyl-CO, halo-$(C_1-C_6)$alkyl-CO— and mono- or di$(C_1-C_6)$alkylamino; e.g. OH, halogen, $(C_1-C_6)$alkyl and $(C_1-C_6)$alkoxy; e.g. OH and $(C_1-C_6)$alkyl;

(12) $R_5$ is phenyl, naphthyl, $(C_3-C_7)$cycloalkyl or 5- or 6-membered heterocyclic ring with one to four heteroatoms each selected independently from N, O and S, e.g. phenyl or $(C_3-C_7)$cycloalkyl, preferably phenyl, or 5- or 6-membered heterocyclic ring with one to four heteroatoms each selected independently from N, O and S (e.g. piperidyl, piperazinyl, morpholinyl, tetrazolyl, pyrrolyl, pyrrolinyl, pyrrolidinyl, thienyl, furyl, oxadiazolyl, pyridazinyl or pyridyl, e.g.

tetrazolyl, oxadiazolyl, thiadiazolyl, piperidinyl, morpholinyl, piperazinyl, pyrrolyl, pyrrolidinyl, pyrrolinyl or pyridyl, such as tetrazolyl, piperazinyl, pyrrolyl, pyrrolidinyl or pyrrolinyl, e.g. piperazinyl, pyrrolyl or pyrrolinyl); each unsubstituted or substituted with one or two $R_6$ as defined above or below;

(13) $R_5$ is e.g. phenyl optionally substituted with one or two, e.g. one, substituent(s) $R_6$ as defined above or below; or $R_5$ is 5-tetrazolyl;

(14) $R_5$ is phenyl, piperidyl, piperazinyl, morpholinyl, tetrazolyl, pyrrolyl, pyrrolinyl, pyrrolidinyl, thienyl, furyl, oxadiazolyl, isoindolinyl, pyridazinyl or pyridyl, e.g. phenyl, tetrazolyl, oxadiazolyl, thiadiazolyl, piperidinyl, morpholinyl, piperazinyl, pyrrolyl, pyrrolidinyl, pyrrolinyl or pyridyl, such as phenyl, tetrazolyl, piperazinyl, pyrrolyl, pyrrolidinyl or pyrrolinyl, e.g. phenyl, piperazinyl, pyrrolyl each unsubstituted or substituted with one or two $R_6$ as defined above or below; or pyrrolinyl substituted with $R_6$ as defined above or below;

(15) each $R_6$ is selected independently from OH, halogen, COOH, 5-tetrazolyl, —NHOH, —CONHOH, —CO—$NH_2$, $NO_2$, SH, $NH_2$, CN, CHO, =O, $(C_1-C_6)$alkyl, $(C_1-C_6)$alkoxy, halo-$(C_1-C_6)$alkyl (e.g. $CF_3$), mono- or di$(C_1-C_6)$alkylamino, —CO—$(C_1-C_6)$alkyl, mono- or di$(C_1-C_6)$alkylamino-CO— and $SO_2R_4$ (wherein $R_4$ is OH, $NH_2$ or mono- or di$(C_1-C_6)$alkylamino, e.g. mono- or di$(C_1-C_6)$alkylamino); e.g. $R_6$ is selected from OH, =O, halogen, COOH, 5-tetrazolyl, —NHOH, —CONHOH, $NO_2$, $NH_2$, CN, CHO, $(C_1-C_6)$alkyl, $(C_1-C_6)$alkoxy, halo-$(C_1-C_6)$alkyl, mono- or di$(C_1-C_6)$alkylamino, —CO—$(C_1-C_6)$alkyl, —CO—$NH_2$ and mono- or di $(C_1-C_6)$alkylamino-CO—; such as from OH, halogen, =O, COOH, 5-tetrazolyl, $NO_2$, $(C_1-C_6)$alkyl, $(C_1-C_6)$alkoxy and halo-$(C_1-C_6)$alkyl; e.g. from OH, =O, COOH, 5-tetrazolyl, $(C_1-C_6)$alkyl and $(C_1-C_6)$alkoxy;

(16) each $R_6$ is selected independently from =O, $(C_1-C_6)$alkyl and $(C_1-C_6)$alkoxy; e.g. =O and $(C_1-C_6)$alkyl;

(17) each $R_6$ is selected independently from OH, halogen, COOH, 5tetrazolyl, NHOH, CONHOH, —CO—$NH_2$, $NO_2$, SH, $NH_2$, CN, CHO, =O, $SO_2R_4$ (wherein $R_4$ is as defined below), $(C_1-C_6)$alkyl, $(C_1-C_6)$alkoxy and halo-$(C_1-C_6)$alkyl (e.g. $CF_3$); e.g. from COOH, 5-tetrazolyl, NHOH, CONHOH, —CO—$NH_2$ and $SO_2R_4$ (wherein $R_4$ is as defined below) e.g. from COOH and 5-tetrazolyl;

(18) t is 1 and $R_2$ is OH, $NO_2$, $SO_2R_4$ (wherein $R_4$ is OH, $NH_2$ or mono- or di$(C_1-C_6)$alkylamino, e.g. mono- or di$(C_1-C_6)$alkylamino), $(C_1-C_6)$alkyl, $NH_2$—$(C_1-C_6)$alkyl, $(C_1-C_9)$alkyl-CO—, halo-$(C_1-C_6)$alkyl-CO—, phenyl-N=N— (unsubstituted or substituted with one to three, e.g. one or two, e.g. one, substituents $R_6$), —$(Y)_n$—$(B)_m$—COOH (e.g. —$(B)_m$—COOH or —Y—B—COOH) or —$(Y)_n$—$(B)_m$—$R_5$, wherein n is 0; or n is 1 and Y is CO; m is 0; or m is 1 and B is $(C_1-C_6)$alkylene, e.g. —$CH_2$—; and $R_5$ is phenyl unsubstituted or substituted with 1, 2 or 3, e.g. one or two, substituent(s) $R_6$ as defined above or below; e.g. with one or two, e.g. one, $R_6$ selected from with COOH or tetrazolyl; or $R_5$ is 5-tetrazolyl, or $R_5$ is piperidinyl, piperazinyl, pyrrolyl, pyrrolinyl or pyrrolidinyl, e.g. piperazin-1-yl, pyrrol-1-yl, pyrrolidin-1-yl or pyrrolin-1-yl, unsubstituted or substituted with one or two $(C_1-C_6)$alkyl or =O, such as 4-$(C_1-C_6)$alkyl-piperazin-1-yl or pyrrole-2,5-dion-1-yl;

(19) $R_5$ is e.g. phenyl substituted with one or two, e.g. one, substituent(s) $R_6$ each selected independently from COOH, 5-tetrazolyl, —CO—$NH_2$, $SO_2R_4$ (wherein $R_4$ is as defined above or below), NHOH and CONHOH, e.g. from COOH and 5-tetrazolyl; or $R_5$ is tetrazolyl, e.g. 5-tetrazolyl;

(20) $R_5$ is e.g. phenyl unsubstituted or substituted with one or two $R_6$ as defined above or below or $R_5$ is tetrazolyl or $R_5$ is piperazinyl, pyrrolyl or pyrrolinyl; each unsubstituted or substituted with one or two OH, =O, $(C_1-C_6)$alkyl, $(C_1-C_6)$alkoxy (such as 4-$(C_1-C_6)$alkyl-piperazin-1-yl or pyrrole-2,5-dion-1-yl);

(21) Y is CO;

(22) B is $(C_1-C_6)$alkylene; and/or

(23) $R_4$ is $(C_1-C_6)$alkyl, $NH_2$, OH or mono- or di$(C_1-C_6)$alkylamino, e.g. $NH_2$, OH or mono- or di$(C_1-C_6)$alkylamino, such as mono- or di$(C_1-C_6)$alkylamino.

A further subgroup of the compounds of formula I' or I are the compounds of formula Ia,

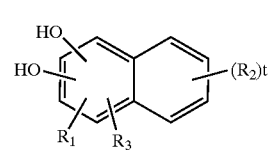

Ia wherein the two OH— substituents are in a position ortho to one another and R1 in a position ortho to one of the hydroxy groups; and $R_1$ to $R_3$ and t are as defined above.

A further subgroup of compounds Ia are compounds of formula Iaa

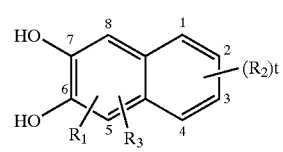

Iaa wherein $R_1$ to $R_3$ and t are as defined above.

Another subgroup of the compounds of formula I' or I are the compounds of formula Ib or Ic,

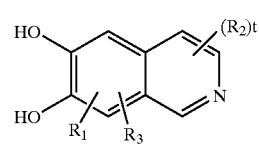

Ib or

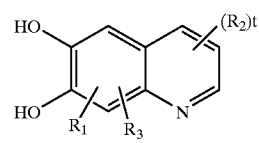

Ic wherein $R_1$ to $R_3$ and t are as defined above.

In a further subgroup of compounds of formula I', I, Ia, Iaa, Ib or Ic, $R_1$ is $NO_2$ CHO or CN, e.g. $NO_2$ or CN, such as $NO_2$; t is 1 or 2, and each $R_2$ is selected independently from $NO_2$, $SO_2R_4$, $(C_1-C_6)$alkyl, $NH_2$—$(C_1-C_6)$alkyl, $(C_1-C_{20})$alkyl-CO—, halo-$(C_1-C_6)$alkyl-CO—, phenyl-N=N— (wherein phenyl is unsubstituted or substituted with one to three, e.g. one or two, e.g. one, substituents $R_6$), —$(Y)_n$—$(B)_m$—COOH (e.g. —$(B)_m$—COOH or —Y—B—

COOH) and —$(Y)_n$—$(B)_m$—$R_5$, wherein n, m, B, Y, $R_4$, $R_5$ and $R_6$ are as defined above. In another subgroup of compounds I', I, Ia, Iaa, Ib or Ic, t is 1 and $R_2$ is $SO_2R_4$, phenyl-N=N— (unsubstituted or substituted with one to three, e.g. one or two, e.g. one, substituent(s) $R_6$), —$(B)_m$—COOH, —Y—B—COOH or —$(Y)_n$—$(B)_m$—$R_5$, n is 0; or n is 1 and Y is CO; m is 0; or m is 1 and $(C_1-C_6)$alkylene; $R_5$ is phenyl, tetrazol-5-yl, piperidin-1-yl, piperazin-1-yl, pyrrol-1-yl, pyrrolidin-1-yl or pyrrolin-1-yl, wherein each of the said rings as $R_5$ can be unsubstituted or substituted with one or two, substituent(s) $R_6$; each $R_6$ is selected independently from OH, halogen, $NO_2$, $(C_1-C_6)$alkyl, $(C_1-C_6)$alkoxy, =O, COOH and 5-tetrazolyl. For example phenyl as $R_5$ can be unsubstituted or substituted with one or two, e.g. one, OH, halogen, $NO_2$, $(C_1-C_6)$alkyl, $(C_1-C_6)$alkoxy, COOH or 5-tetrazolyl, e.g. COOH or 5-tetrazolyl; A heterocyclyl as $R_5$ can be e.g. 5-tetrazolyl; or piperidin-1-yl, piperazin-1-yl, pyrrol-1-yl, pyrrolidin-1-yl or pyrrolin-1-yl, e.g. piperazin-1-yl or pyrrol-1-yl, each optionally substituted with $R_6$ as defined above, e.g. with $(C_1-C_6)$ alkyl, $(C_1-C_6)$alkoxy or =O, (such as 4-$(C_1-C_6)$alkyl-piperazin-1-yl or pyrrole-2,5-dion-1-yl).

In another subgroup of the compounds I', I, Ia, Iaa, Ib or Ic, t is 1 or 2 and $R_2$ or, resp., at least one of $R_2$ is OH, halogen, $(C_1-C_6)$alkyl, $(C_2-C_6)$alkenyl, $(C_1-C_6)$alkoxy, $NH_2$—$(C_1-C_6)$alkyl, —CO—$(C_1-C_9)$alkyl, phenyl-N=N— (unsubstituted or substituted with one to three, e.g. one or two, e.g. one, substituent(s) $R_6$) or —$(Y)_n$—$(B)_m$—$R_5$, wherein n, m, B, Y, $R_5$ and $R_6$ are as defined above, e.g. $R_2$ is OH, $(C_1-C_6)$alkyl or or —$(Y)_n$—$(B)_m$—$R_5$, wherein n is 0, m is 0 and $R_5$ is phenyl unsubstutited or optionally substituted with OH, halogen, $(C_1-C_6)$alkyl or $(C_1-C_6)$ alkoxy.

In a further subgroup of the compounds of formula Ia, Iaa, Ib or Ic, $R_3$ is H, $R_1$ is at 5-position (according to the numbering depicted in formula Iaa). In another subgroup of compounds Ia, Iaa, Ib or Ic, t is 0, or t is 1 or 2, e.g. one. Yet in another subgroup of compounds Ia or Iaa, $R_2$ (or one of $R_2$) is at 2-position.

The compounds of formula I' and the subgroups I, Ia, Iaa, Ib and Ic, as well as the pharmaceutically acceptable salts and the pharmaceutically acceptable esters thereof, are referred to below as the compounds of the invention, unless otherwise indicated.

The compounds of the invention may have chiral carbon atom(s) in their structure. The invention includes within its scope all the possible stereoisomers of the compounds I, including geometric isomers, e.g. Z and E isomers (cis and trans isomers), and optical isomers, e.g. diastereomers and enantiomers. Furthermore, the invention includes in its scope both the individual isomers and any mixtures thereof, e.g. racemic mixtures. The individual isomers may be obtained e.g. using the corresponding isomeric forms of the starting material or they may be separated after the preparation of the end compound according to conventional separation methods. For the separation of i.a. optical isomers, e.g. enantiomers, from the mixture thereof the conventional resolution methods, e.g. fractional crystallisation, may be used.

Physiologically acceptable salts may be prepared by known methods. The pharmaceutically acceptable salts are the usual organic and inorganic salts in the art. Furthermore, any COOH—, OH— and/or amino-functionality, such as COOH— and/or OH— functionality, e.g. COOH— functionality, when present in the compounds of the invention, can be converted to a pharmaceutically acceptable ester or, respectively, a pharmaceutically acceptable amide in a manner known in the art using a pharmaceutically acceptable acid or, respectively, a pharmaceutically acceptable alcohol known from the literature. Examples of such pharmaceutically acceptable acids and alcohols are e.g. aliphatic (e.g. $C_1-C_9$, such as $C_1-C_6$) acids and alcohols, or aromatic acids and alcohols, which are conventional in the field of pharmaceuticals and which retain the pharmacological properties of the free form.

Pharmaceutically acceptable salts include, when possible, also acid addition salts conventionally used in the art.

Terms employed herein have the following meanings: A halogen or halo refers to fluorine, chlorine, bromine or iodine. The term $(C_1-C_6)$alkyl as employed herein as such or as part of another group includes both straight and branched chain radicals of up to 6 carbon atoms, preferably of 1, 2, 3 or 4 carbon atoms. In CO—$(C_1-C_{20})$alkyl or CO—$(C_1-C_9)$ alkyl the alkyl moiety includes both straight and branched chain radicals of up to 20 or, resp., 9 carbon atoms, preferably of up to 6 carbon atoms, e.g. 1, 2, 3 or 4 carbon atoms. The term $(C_1-C_6)$alkoxy as such or as part of another group refers to —O$(C_1-C_6)$alkyl, wherein $(C_1-C_6)$alkyl is as defined above. The term $(C_2-C_6)$alkenyl includes both straight and branched chain radicals of up to 6 carbon atoms, preferably of 2, 3 or 4 carbon atoms, containing double bond(s), e.g. one double bond. The term halo-$(C_1-C_6)$alkyl as such or as part of another group refers to $(C_1-C_6)$alkyl radical, as defined above, that is substituted by one or more halo radicals as defined above, e.g. trifluoromethyl, difluoromethyl etc. The term $(C_1-C_6)$alkylene refers to a straight or branched, saturated hydrocarbon chain divalent radical, e.g. methylene, ethylene, propylene, butylene and the like. The term $(C_2-C_6)$alkenylene refers to a straight or branched, unsaturated hydrocarbon chain divalent radical, wherein the unsaturation is present as one or more, e.g. one, double bond(s), e.g. vinylene, propenylene, butenylene etc. The term $(C_3-C_7)$cycloalkyl refers to a monocyclic 3- to 7-membered saturated carbocyclic ring, i.e. cyclopropyl, cyclobutyl, cyclopentyl, cyclohexyl or cycloheptyl ring. The 5- to 10-membered heterocyclyl with one to four heteroatoms selected independently from N, O and S means a mono- or bicyclic 5- to 10-membered, e.g. monocyclic 5- or 6-membered, partially or fully saturated, or aromatic hetero ring system. Examples of such heterocyclyls include piperidinyl, piperazinyl, morpholinyl, pyrrolyl, pyrrolinyl, pyrrolidinyl, isoindolinyl, tetrahydropyridyl, dihydropyridyl, pyridyl, pyrazinyl, pyrimidinyl, pyridazinyl, thienyl, furyl, thiazolyl, oxadiazolyl, thiadiazolyl, tetrazolyl etc., such as tetrazolyl, e.g. 5-tetrazolyl, piperidinyl, piperazinyl, morpholinyl, pyrrolyl, pyrrolinyl and pyrrolidinyl.

In case of di$(C_1-C_6)$alkylamine, the $(C_1-C_6)$alkyl chains can be identical or different.

It is evident to a skilled person that in the compounds I', I, Ia, Iaa, Ib or Ic the nature of the optional substituent(s) $R_6$ and the maximal possible number thereof in a ring $R_5$ depend on the nature of the ring $R_5$. E.g. the option =O as $R_6$ is possible only for $(C_3-C_7)$cycloalkyl or saturated or partially saturated heterocyclic rings as $R_5$, wherein a double bond can be formed between the ring atom of $R_5$ and the said oxygen atom.

The compounds of the invention can be prepared by a variety of synthetic routes analogously or according to the methods known in the literature using suitable starting materials.

In general, the compounds of formula Iaa, wherein $R_3$ is H, $R_1$ is e.g. $NO_2$, t is 1 and $R_2$ is at 2-position can be prepared e.g. analogously or according to scheme 1:

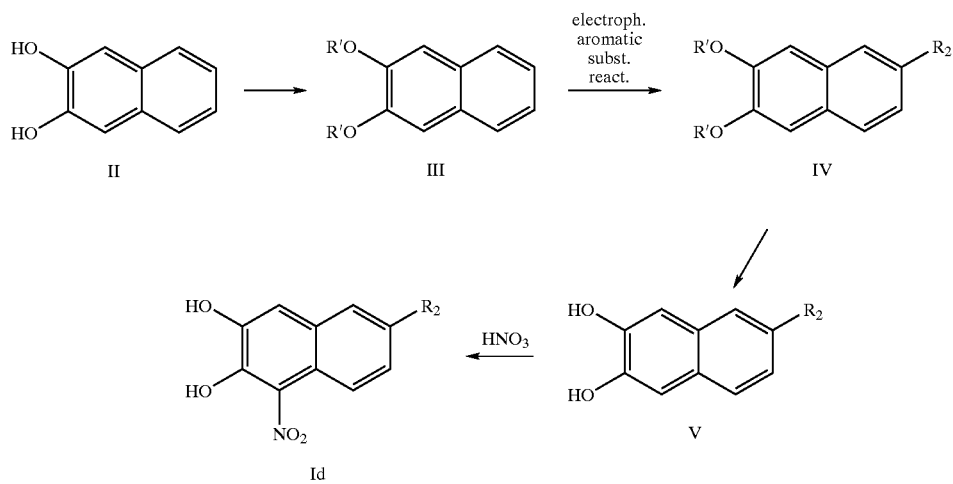

wherein $R_2$ is as defined above, each R' is a conventional protecting group for hydroxy, e.g. $(C_1–C_6)$alkyl, e.g. methyl.

According to the scheme 1 the hydroxy groups of a compound II are protected in a conventional manner. Then a substituent $R_2$ is introduced to the protected compound III by an electrophilic aromatic substitution reaction in a manner known in the art. By the term "electrophilic aromatic substitution reaction" the usual reactions known in the art are meant, e.g. nitration, nitrosation, diazonium coupling, sulfonation, halosulfonation, halogenation, Friedel-Crafts alkylation and acylation, formylation by Vilsmeier, haloalkylation and acylation by Hoesch-reaction just to mention the most known reactions. The compound IV thus obtained is deprotected, and the deprotected product V is nitrated using e.g. diluted nitric acid in a suitable solvent, e.g. at $(-20)°$ C.$–0°$C., to obtain an end compound Id.

The substituent $R_2$ can be converted, if desired, to another functionality of the invention in different stages of the preparation of the end compounds in a manner known to a skilled person, e.g. before or after the introduction of $R_1$. The following schemes 2 and 3 illustrate e.g. a further elaboration of the $R_2$ substituent before the introduction of $R_1$.

SCHEME 2

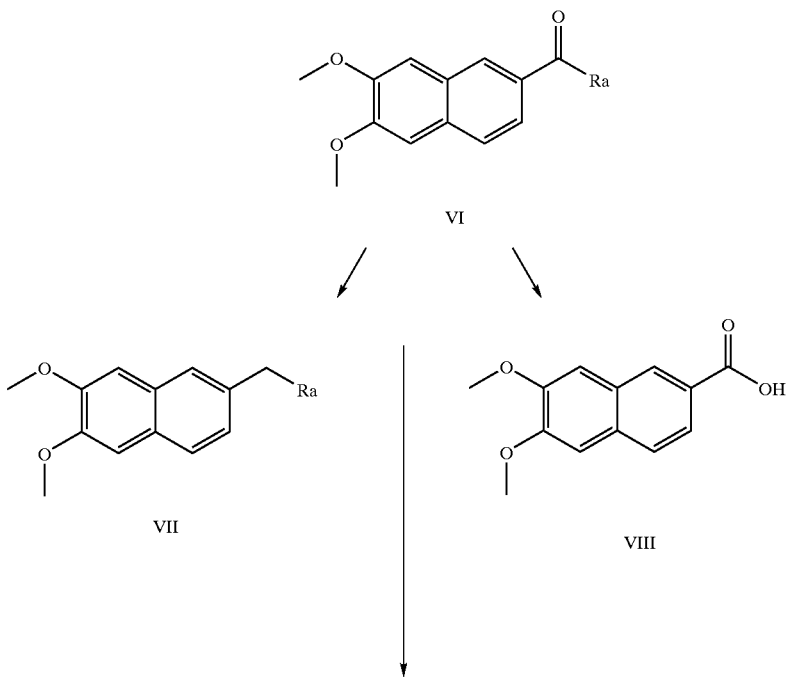

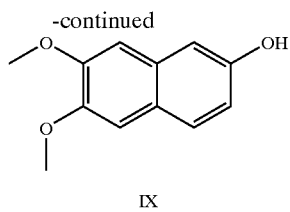

IX

SCHEME 3

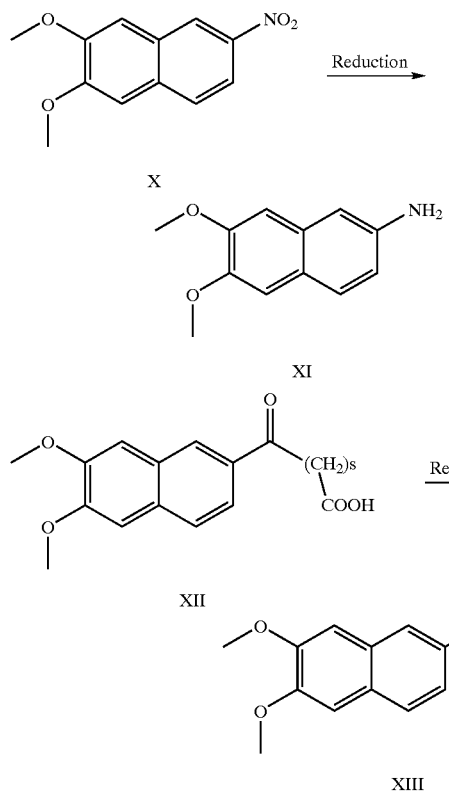

The preparation of compounds Ib and Ic are illustrated in scheme 4 with specific examples:

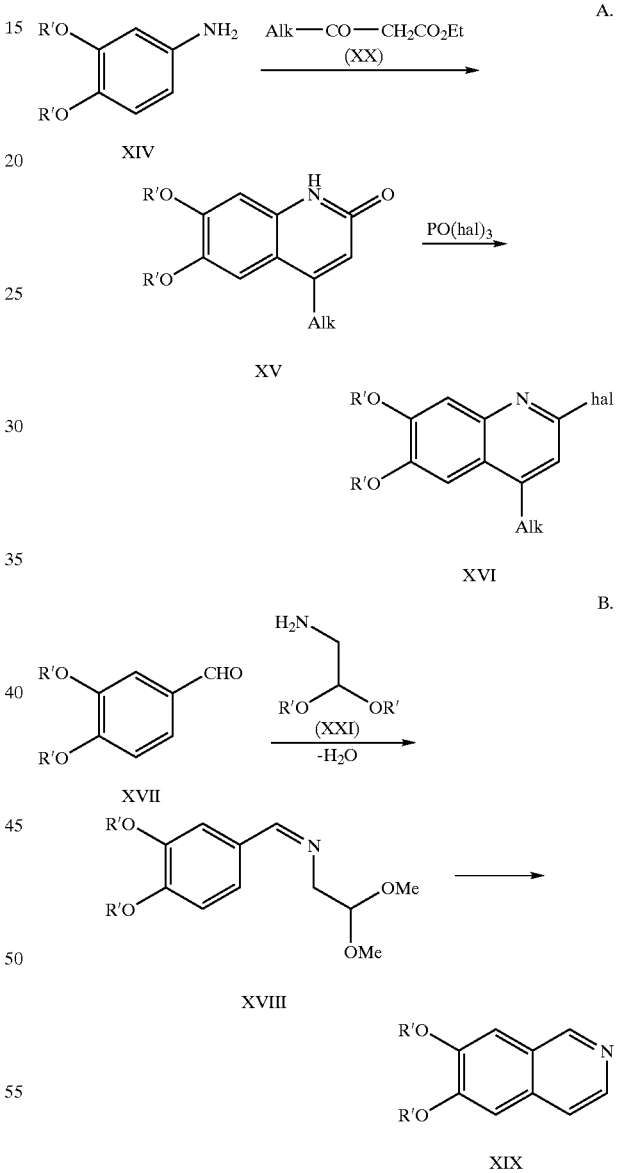

According to scheme 2, a protected compound VI (wherein $R_2$ is —CO—Ra, Ra is alkyl, e.g. $(C_{1-5})$alkyl, and, e.g. for the preparation of the specific compounds VIII and IX, Ra is methyl) produced e.g. according to the method of scheme 1 (cf. compound IV) can be subjected to a conventional reduction step to obtain a compound VII (wherein $R_2$ is —CH$_2$—Ra, Ra is alkyl, e.g. $(C_{1-5})$alkyl, e.g. methyl), to a known hypobromite reaction to obtain a compound VIII (wherein $R_2$ is —COOH) or to a known Dakin reaction to obtain compound IX (wherein $R_2$ is OH).

According to scheme 3, a compound X (wherein $R_2$ is NO$_2$) or XII (wherein $R_2$ is —CO—(CH$_2$)s—COOH, s is 1 to 5) produced e.g. according to the method of scheme 1 (cf. compound IV) can both be subjected to a reduction step to obtain a compound XI (wherein $R_2$ is NH$_2$) or, respectively, compound XII (wherein $R_2$ is —CH$_2$—(CH$_2$)s—COOH, s is 1 to 5). The both reduction reactions are known in the chemical field.

Subsequently, the substituent $R_1$, e.g. a nitro group, is then introduced (e.g. after a deprotection step) to an intermediate compound VI, VII, VIII, IX, XI or XIII to obtain an end compound of the invention. If desired, further optional substituents of the invention can also be introduced to the above intermediate compounds before or after the introduction of $R_1$.

wherein R' is a conventional protecting group for hydroxy, e.g. $(C_1-C_6)$alkyl, e.g. methyl, Alk is $(C_1-C_6)$alkyl, e.g. methyl, and hal is halogen, e.g. Cl.

Compounds Ic of scheme 4A, wherein $R_3$ is H, t is 2 and one of $R_2$ is $(C_1-C_6)$alkyl, e.g. methyl, and the other is halogen, e.g. Cl, can be prepared according to the known Conrad-Limpach reaction procedure by reacting compound XIV with a compound XX in a suitable solvent and in an elevated temperature to obtain compound XV. Compound XV is then treated with PO(hal)3 to obtain compound XVI, which is deprotected and wherein the substituent $R_1$, e.g. a nitro group, is introduced in a manner known in the art to obtain an end compound Ic. Furthermore, compounds Ib of scheme 4B, wherein $R_3$ is H and t is 0, can be prepared according to a procedure known as Pomeranz-Fritsch synthesis, i.e. by reacting compound XVII with a compound XXI in a suitable solvent and reaction conditions to obtain compound XVIII which is then cyclized in acidic conditions to result in compound XIX. Compound XIX can then be deprotected and a substituent $R_1$, e.g. a nitro group, be introduced in a manner known in the art to obtain an end compound Ic.

Examples of other synthetic routes which can be used for the preparation of compounds Ib and Ic of the invention i.a. Pictet-Spengler and Bischler-Napieralski synthesis (for the preparation of compounds Ib) and Doebner-Miller and Doebner synthesis (for the preparation of compounds Ic) can be mentioned.

The starting material II, XIV, XVII, XX, XXI and other used reagents are commercially available or can be prepared via a variety of known synthetic routes known in the literature or as described above or below.

It is obvious to a skilled person that, in the above reactions, any starting material or intermediate can be protected, if necessary, in a manner well known in the chemical field. Any protected functionality is subsequently deprotected in a usual manner.

It should be noted that the above described synthetic routes are meant to illustrate the preparation of the compounds of the invention and the preparation is by no means limited thereto, i.e. other synthetic methods which are within the general knowledge of a skilled person are also possible.

The compounds of the invention may be converted, if desired, into their pharmaceutically acceptable salt or ester form using methods well known in the art.

As already mentioned hereinbefore, the compounds of the invention show interesting pharmacological properties, namely they exhibit catechol-O-methyltransferase (COMT) enzyme inhibiting activity. The said activity of the compounds of the invention is demonstrated with the pharmacological tests presented below.

EXPERIMENT I: Determination of COMT activity ($IC_{50}$)

The determination of $IC_{50}$ was performed by measuring the COMT activity in a test sample which contained S-COMT enzyme (about 30 nM), 3 mM dopamine (as the substrate of COMT), 5 mM magnesium chloride, 0.05 mM S-adenosyl-L-methionine (AdoMet) and a test compound of the invention at various concentrations in 0.1 M phosphate buffer, pH 7.4, at 37° C.

The reaction in the test sample was initiated by adding the dopamine substrate to the sample mixture and, after incubation for 15 min at 37° C., the reaction was stopped with 4 M perchloric acid and stabilized further 10 min in ice bath. Thereafter the precipitated proteins were removed by centrifugation (4000×G for 10 min). The activity of COMT enzyme was measured by determining the concentration of the reaction products, 3-methyldopamine and 4-methyldopamine, by HPLC. The results were calibrated with 3-methyldopamine standards. See also T. Lotta et al., Biochemistry, vol.34(13), 1995, p.4204. The $IC_{50}$ value is the concentration of the test compound which causes a 50% decrease in COMT activity. The results are shown in table 1.

TABLE 1

| The compound of example no. | IC50 (nM) |
| --- | --- |
| Example 1 | 30 |
| Example 3 | 80 |
| Example 4 | 25 |
| Example 5 | 45 |
| Example 7 | 30 |
| Example 8 | 200 |
| Example 9 | 80 |
| Example 10 | 15 |
| Example 11 | 25 |
| Example 13 | 100 |
| Example 14 | 15 |
| Example 15 | 140 |

Particularly, the compounds of the invention have preferable COMT inhibiting properties as therapeuticals. Accordingly, they can be used for the treatment of diseases or conditions wherein COMT inhibitors are indicated to be useful, i.a. in the treatment of Parkinson's disease e.g. for the potentiation of levodopa (+DDC) therapy.

The compounds of the invention may be administered enterally, topically or parenterally.

The compounds of the invention may be formulated alone or together with one or more active agents and/or together with a pharmaceutically acceptable excipient in different pharmaceutical unit dosage forms, e.g. tablets, capsules, solutions, emulsions and powders etc., depending on the route of adminstration, using conventional techniques. The pharmaceutically acceptable excipient can be selected from those conventionally used in the field of pharmaceuticals noticing the chosen route of administration.

The amount of the active ingredient varies from 0.01 to 100 weight-% depending on i.a. the type of the dosage form.

The specific dose level of the compounds of the invention depends, of course, on several factors such as the compound to be administered, the species, age and the sex of the subject to be treated, the condition to be treated and on the route and method of administration. For example, the compounds of the invention may administered from 0.5 µg/kg to 100 mg/kg per day for an adult male.

The present invention also provides a compound of the invention or an ester or salt thereof, or a pharmaceutical composition thereof, for use in a method of treatment of human or animal body.

The present invention further provides a compound of the invention or an ester or salt thereof, as well as a pharmaceutical composition thereof, for use as a COMT inhibitor, i.a. for the treatment of diseases and conditions where inhibition of COMT enzyme is useful, e.g. for the treatment of Parkinson's disease. The use of the compounds of the invention for the manufacture of a medicament to be used for the above indications is also provided. The invention further relates to a method for the treatment of above indicated conditions or diseases, by administering to a subject in need of such treatment an effective amount of the compound of the invention or a pharmaceutically acceptable ester or salt thereof.

The present invention will be explained in more detail by the following examples. The examples are meant only for illustrating purposes and do not limit the scope of the invention which is defined in claims. The used starting material and reactants are commercially available.

EXAMPLE 1

1-Nitronaphthalene-2,3-diol, Method A

Fuming nitric acid (4.2 ml) was added to methylene chloride (50 ml) and the resulting solution diluted with diethyl ether (100 ml): Then 3-methylbuthylnitrite (1.9 ml) was added and this final solution added at 25–30° C. to a solution of 2,3-dihydroxynaphthalene (16.0 g) in ether (100 ml).The reaction mixture was washed with water, extracted into potassium bicarbonate (1 M), acidified and finally extracted into ether. After column chromatography (SiO2, toluene-ethyl acetate-acetic acid 18:1:1) the product was crystallized from toluene. Yield: 1.5 g, melting point 141–143° C.

$^1$H-NMR (DMSO-$d_6$, 400 MHz): 7.35 (s, 1H), 7.36–7.45 (m, 3H), 7.77 (dd, 1H, J=7 Hz, n. 1 Hz), 10.8 (br s, 2H).

EXAMPLE 2

1-Nitronaphthalene-2,3-diol, Method B (a) Naphthalene-2,3-diol Cyclohexylidene Ketal The solution of naphthalene 2,3-diol (48.0 g), cyclohexanone and toluene sulfonic acid hydrate (1.0 g) in toluene (200 ml) was refluxed with water separation (Dean-Stark) for 45 minutes. After washing with sodium hydroxide (1 M, 300 ml) the organic phase was dried, evaporated and crystallized from heptane. Yield: 40.8 g.

$^1$H-NMR (DMSO-$d_6$, 400 MHz): 1.46–1.53 (m, 2H), 1.66–1.73 (m, 4H),1.92 (t, 4H, j =6 Hz), 7.21 (s, 2H), 7.26–7.31 (m, 2H), 7.66–7.71 (m, 2H).

(b) 1-Nitronaphthalene-2,3-diol

To a solution of the product from the previous step (a) (14.4 g) in methylene chloride (150 ml) a solution of fuming nitric acid (2.8 ml) in methylene chloride (33 ml) was added at 15–20° C. After 30 min methanesulfonic acid (70 ml) was added and the solution was boiled for two hours. The cooled reaction mixture was poured into ice water (600 ml). The organic phase was separated and washed with water. The product was extracted and purified as described in the previous example 1. Yield: 3.0 g. Physical characteristics as above.

EXAMPLE 3

(6,7-Dihydroxy-5-nitro-naphthalen-2-yl)-phenyl-methanone (a) (6,7-Dimethoxy-naphthalen-2-yl)-phenyl-methanone Aluminum chloride (16.0 g) was added to a solution of 2,3-dimethoxynaphthalene (18.0 g) and benzoylchloride (12.0 g) in cold methylene chloride (400 ml) and the solution was stirred overnight. After treatment with cold water the phases were separated and the methylene chloride phase washed with 1 M sodium hydroxide. The product was triturated with warm ether. Yield: 7 g, melting point 124–125° C.

$^1$H-NMR (DMSO-$d_6$, 400 MHz): 8.17(s, 1H), 7.9 (d, 1H, J=9 Hz), 7.18 (d,2 H, J=Hz), ,72 (dd, 2H, 7, 1.5 Hz), 7,68 (d, 1H, J=9 Hz), 7.59 (dd,2H, J=7, 6.5 Hz), 7.53 (s,1H), 7.43 (s,1H), 3.94 (s,3H), 3.89 (s,3H).

(b) (6,7-Dihydroxy-naphthalen-2-yl)-phenyl-methanone

The product from the previous step (a) (5 g) was heated in pyridinium hydrochloride (30 g) at 220° C. for 15 minutes, cooled to 150–160° C., poured into ice water filtered and washed with water. Yield: 4.2 g, melting point 176–193° C.

$^1$H-NMR (DMSO-$d_6$, 400 MHz): 10 (b,1H, OH), 9.8 (b,1H, OH),8.01 (s,1H), 7.67–7.77 (m,3H), 7.57–7.59 (m,2H), 7.27 (s, 1H) 7.23 (s,1H).

(c) (6,7-Dihydroxy-5-nitro-naphthalen-2-yl)-phenyl-methanone

The product from the previous step (b) (2.64 g) was slurried in ether (100 ml), N,N-dimethylacetamide (3 ml) added and the resulting solution cooled to 0° C. Nitric acid in methylene chloride (2 M, 5 ml) was gradually added and then stirred 30 minutes at ambient temperature. The reaction mixture was evaporated, triturated with water and decanted. The resulting oil was dried in the oven and then purified by column chromatography (SiO$_2$, toluene-THF-acetic acid 8:1:1.The product was finally triturated with methyl-t-buthyl ether. Yield: 0.18 g, melting point 196–205° C.

$^1$H-NMR (DMSO-$d_6$): 11.3 (b,2H, OH), 7.96 (d,1H, J=8 Hz), 7.82 (s,1H), 7.68–7.78 (m,5H), 7.57–7.61 (m,2H) 7.46 (s,1H).

EXAMPLE 4

1-(6,7-Dihydroxy-5-nitro-naphthalen-2-yl)-2-methyl-propan-1-one (a) 1-(6,7-Dimethoxy-naphthalen-2-yl)-2-methyl-propan-1-one The solution of 2,3-dimethoxynaphthalene (16.5 g ), isobutyroylchloride (12.5 g) and aluminum chloride (15.7 g) in methylene chloride (200 ml) was stirred at ambient temperature overnight. The solution was then washed with saturated sodium bicarbonate and water, dried with sodium sulfate and evaporated. Finally the crude product was triturated with ether. Yield: 13.5 g, melting point 103–105° C.

$^1$H-NMR (DMSO-$d_6$): 8.51 (s,1H), 7.83 (s,2H), 7.53 (s,1H), 7.39 (s,1H), (s,3H). 3.91 (s,3H), 3.76–3.80 (m,1H), 1.16 (d,6H, J=8 Hz).

(b) 1-(6,7-Dihydroxy-naphthalen-2-yl)-2-methyl-propan-1-one

The product from the previous step (a) (13.5 g) and pyridinium hydrochloride (100 g) were heated at 220–225° C. for 30 minutes. The reaction mixture was treated with water and extracted with ether. The crude product was triturated with petroleum ether (40–60° C.).Yield: 11.2 g, melting point 154–156° C.

$^1$H-NMR (DMSO-$d_6$): 9.9 (b,2H,OH), 8.35 (s,1H), 7.65–7.71 (m,2H), 7.32 (s,1H), 7.17 (s,1H), 3.74–3.79 (m,1H), 1.14 (d,6H, J=7 Hz).

(c) 1-(6,7-Dihydroxy-5-nitro-naphthalen-2-yl)-2-methyl-propan-1-one

Nitric acid in methylene chloride (2 M, 1.4 ml) was gradually added to the solution of the product from the previous step (b) (0.65 g) in ethyl acetate (10 ml) at −10° C. After 20 min at 0° C. the solvents were evaporated. FLASH-chromatography on silica with toluene-ethyl acetate-acetic acid 8:1:1 as the solute and then trituration with ether-petroleum ether (40–60° C.) yielded the raw product which was finally recrystallized from ethyl acetate-heptane. Yield: 0.13 g, melting point 197–204° C.

$^1$H-NMR (DMSO): 11.3 (b,2H,OH), 8.05 (s,1H), 7.90 (m,2H), 7.42 (s,1H), 3.68–372 (m,1H), 1.14 (d,6H, J=7 Hz).

EXAMPLE 5

6-Isobutyl-1-nitro-naphthalene-2,3-diol

Sodium borohydride (0.55 g) was added to a solution of the product from example 4(c) (0.33 g) in trifluoroacetic acid (11 ml). The reaction mixture was stirred at ambient temperature for two hours, poured into water, extracted with ethyl acetate, dried, evaporated and recrystallized from ethanol-water. Yield: 0.22 g, melting point 105–108° C.

$^1$H-NMR (DMSO-$d_6$): 10.68 (b,2H,OH), 7.69 (d,1H, J=8 Hz), 7.31 (s,1H), 7.20 (d,1H, J=8 Hz), 7.15 (s,1H), 2.52–2.55 (m,2H), 1.84–1.87 (m,1H), 0.85–0.87 (m,6H).

EXAMPLE 6

1-(6,7-Dihydroxy-5-nitro-naphthalen-2-yl)-pentadecan-1-one (a) 1-(6,7-Dimethoxy-naphthalen-2-yl)-pentadecan-1-one The solution of 2,3-dimethoxynaphthalene (1.9 g), palmitoyl chloride (3.2 ml) and aluminium chloride (1.5 g) in methylene chloride (40 ml) was stirred at ambient temperature overnight. The reaction mixture was worked up as described in example 4(a). The crude product was recrystallized from ethyl acetate-heptane. Yield 2.0 g.

$^1$H-NMR (CDCl$_3$): 8.33 (d,1H, J=1.5 Hz), 7.90 (dd,1H, J=8.8 and 1.5 Hz), 7.72 (d,$_1$H, J=8.8 Hz), 7.23 (s,1H), 7.14 (s,1H), 4.02 (s,3H), 4.03 (s,3H), 3.05 (2H, J=7.4 Hz), 1.78 (m,2H), 1.25–1.45 (m, 24H), 0.88 (t,3H, J=7 Hz).

(b) 1-(6,7-Dihydroxy-naphthalen-2-yl)-pentadecan-1-one

The product from the previous step (a) (3.6 g) and pyridinium hydrochloride (36 g) were heated for one hour at 220° C. Work-up as described in example 3(b). Yield: 2.7 g, melting point 133–134° C.

$^1$H-NMR (DMSO-d$_6$): 9.97 (s,1H,OH), 9.78 (s,1H,OH), 8.32 (s,1H), 7.62–7.70 (m,2H), 7.30 (s,1H), 7.16 (s,1H), 3.03–3.07 (m,2H), 1.61–1.65 (m,2H),1.23–1.3 (m,24H), 0.83–0.86 (m,3H).

(c) 1-(6,7-Dihydroxy-5-nitro-naphthalen-2-yl)-pentadecan-1-one OR-1770

Nitric acid in methylene chloride (2 M, 3.5 ml) was gradually added to a solution of the product from the previous step (b) (2.8 g) in ethyl acetate (500 ml) at 0° C. The reaction mixture was stirred at room temperature overnight and then at 50° C. for two hours. After evaporation the product was purified by column chromatography as described in example 4(c). The crude product was recrystallized from ethyl acetate and triturated with ether. Yield: 0.1 g, melting point 128–130° C.

$^1$H-NMR (DMSO-d$_6$): 11.2 (b,2H), 8.04 (s,1H), 7.88 (s, 2H), 7.41 (s, 1H),3.02–3.06 (m,2H), 1.58–1.63 (m,2H), 1.15–1.36 (m,24H), 0.82–0.86 (m,3H).

EXAMPLE 7

6,7-Dihydroxy-5-nitro-naphthalene-2-carboxylic Acid (a) 6,7-Dimethoxy-naphthalene-2-carboxylic Acid Bromine (4.6 ml) was added to sodium hydroxide solution (2.5 M, 130 ml) at 0° C. After 5 minutes on ice the solution was warmed to 35° C. Then a solution of the product from example 3(a) (4.6 g) in dioxane (30 ml) was added. The reaction mixture was stirred 20 min at 35° C., cooled to 21–23° C. and then a bisulphite solution (4 g Na$_2$S$_2$O$_5$ in 40 ml water) added. After 30 minutes at 23° C. water (200 ml) was added and the reaction mixture was once washed with methylene chloride (100 ml). The water phase was separated and kept on ice for an hour, filtered and washed with water. Yield: 4.2 g, melting point 256–258° C.

$^1$H-NMR (DMSO-d$_6$): 12.82 (s,1H,COOH), 8.45 (s,1H), 7.78–7.83 (m,2H), 7.49 (s,1H), 7.36 (s,1H), 3.91 (s,3H), 3.90 (s,3H).

(b) 6,7-Dihydroxy-naphthalene-2-carboxylic Acid

The product from the previous step (a) (2 g) and pyridine hydrochloride (12 g) were heated at 220° C. for 15 minutes. The reaction mixture was worked up with acidic water (pH 2–3), filtered and washed with water. Yield: 1.6 g, melting point 241–250° C.

$^1$H-NMR (DMSO-d$_6$): 12.67 (b,1H,COOH), 9.95 (s,1H, OH), 9.75(s,1H,OH), 8.26. (s,1H), 7.62–7.69 (m,2H), 7.26 (s,1H), 7.17 (s,1H).

(c) 6,7-Dihydroxy-5-nitro-naphthalene-2-carboxylic Acid

Nitric acid in methylene chloride (2 M, 2.5 ml) was gradually added to a solution of the product from the previous step (b) (1 g) in acetone (10 ml) at 0° C. and stirred for an hour at that temperature. The reaction mixture was worked up as described in example 6(c). The purified product was finally recrystallized from ether. Yield: 0.1 g, melting point over 310° C.

$^1$H-NMR (DMSO-d$_6$): 12.7–13.3 (b,1H,COOH), 11–11.5 (b,2H;OH), 8.07 (s,1H),7.83–7.89 (m,1H), 7.42 (s,1H).

EXAMPLE 8

2,3-Dihydroxy-naphthalene-1-carbaldehyde

Phosphorous oxychloride (1.9 ml) was added to a solution of 2,3-dihydroxynaphthalene (3.2 g) in DMF (26 ml) at 0° C. The reaction mixture was kept for four hours at 100° C. Water (50 ml) was added to the cooled mixture and the resulting oily suspension refluxed for 20 min. The cool reaction mixture was poured into ice, filtered, washed with water and recrystallized from 2-propanol-water. Yield: 0.1 g, melting point 129–134° C.

$^1$H-NMR (DMSO-d$_6$): 10.5–12 (b,2H,OH), 10.82 (s,1H, CHO), 8.76 (d,1H, J=8 Hz), 7.71 (dd,1H, J=8 and 1 Hz), 7.47 (s,1H), 7.35–7.44(m,2H).

EXAMPLE 9

1-(6,7-Dihydroxy-5-nitro-naphthalen-2-yl)-heptan-1-one (a) 1-(6,7-Dimethoxy-naphthalen-2-yl)-heptan-1-one Aluminium chloride (2.66 g) was added to a solution of: heptanoylchloride (3.1 ml) and 2,3-dimethoxynaphthalene (3.76 g) in methylene chloride (50 ml) at 0° C. The reaction mixture was stirred at room temperature overnight and then worked up as described in example 3(a). The crude product was recrystallized from ethanol. Yield: 2.8 g, melting point 77–78° C.

$^1$H-NMR (DMSO-d$_6$, 400 MHz): 8.49 (s,1H), 7.81 (s,2H), 7.51 (1H); 7.18 (s,1H) 3.92 (s,3H), 3.91 (s,3H), 3.07 (t,2H, J=8 Hz), 1.61–1.68 (m,2H), 1.29–1.37 (m,8H), 0.87 (t,3H, J=8 Hz).

(b) 1-(6,7-Dihydroxy-naphthalen-2-yl)-heptan-1-one

The product from the previous step (a) (2.6 g) and pyridinium hydrochloride (34 g) were heated at 225° C. for 20 minutes. The reaction mixture was allowed to cool to 150–160° C. and then poured into ice. The crude product was taken in 2-propanol and precipitated with water. Yield: 2.0 g.

$^1$H-NMR (DMSO-d$_6$, 400 MHz): 9.99 (s,1H,OH), 9.80 (s,1H,OH), 8.34 (s,1H), 7.64–7.71 (m,2H), 7.32 (s,1H), 7.18 (s,1H), 3.07 (t,2H, J=8 Hz), 1.61–1.68 (m,2H), 1.31–1.35 (m,8H), 0.88 (m,3H).

(c) 1-(6,7-Dihydroxy-5-nitro-naphthalen-2-yl)-heptan-1-one

Nitric acid in methylene chloride (2 M, 2.5 ml) was gradually added to a solution of the product from the previous step (b) (1.36 g) in ethyl acetate (80 ml) at 0° C. The reaction mixture was worked up as described in example 4(c). The crude product was recrystallized from toluene. Yield: 50mg, melting point 97–98° C.

¹H-NMR (DMSO-d$_6$, 400 MHz): 11.22 (b,2H,OH), 8.04 (s,1H), 7.88 (s,1H), 7.41 (s,1H), 3.04 (t,2H, J=8 Hz), 1.60–1.63 (m,2H), 1.27–1.32 (m,8H), 0.86 (m,3H)

EXAMPLE 10

1,6-Dinitro-naphthalene-2,3-diol (a) Acetic Acid 3-hydroxy-naphthalen-2-yl Ester Acetylchloride (0.71 ml) was added to a solution of 2,3-dihydroxynaphthalene (1.6 g) and pyridine (0.81 ml) in ethyl acetate (20 ml) at 0° C. The mixture was stirred for few hours at room temperature and then washed with water, dried and evaporated to dryness. The crude product was recrystallized from ether. Yield: 0.52 g.

¹H-NMR (DMSO-d$_6$, 400 MHz): 10.09 (s,1H,OH), 7.71–7.77 (m,2H), 7.57 (s,1H), 7.38–7.41 (m,1H), 7.28–7.32 (m,1H), 7.27 (s,1H), 2.31 (s,3H).

(b) Acetic Acid 3-hydroxy-4,7-dinitro-naphthalen-2-yl Ester

Nitric acid in methylene chloride (2 M, 2.9 ml) was gradually added to a solution of the product from the previous step (a) (0.5 g) in ethyl acetate (20 ml) at 0° C. The mixture was stirred an additional half an hour at room temperature, cooled to 0° C. and filtered. Yield: 0.39 g.

¹H-NMR (DMSO-d$_6$, 400 MHz): 9.01 (s,1H), 8.32 (d,1H, J=8 Hz), 8.28 (s,1H), 7.79 (d,1H, J=8 Hz), 2.40 (s,3H).

(c) 1,6-Dinitro-naphthalene-2,3-diol

Two drops of concentrated hydrochloric acid was added to a solution of the product from the previous step (b) (0.37 g) in methanol (20 ml) and this solution stirred for 16 hours at 50° C. Methanol was evaporated and the rest triturated with ether. Yield: 0.11 g, melting point 200–207° C.

¹H-NMR (DMSO-d$_6$, 400 MHz): 10.8–12 (b,2H,OH), 8.89 (s,1H), 8.12 (d,1H, J=4 Hz), 7.68 (s,1H), 7.65 (d,1H, J=4 Hz).

EXAMPLE 11

6,7-Dihydroxy-5-nitro-naphthalene-2-sulfonic Acid Dipropylamide (a) 6,7-Dihydroxy-naphthalene-2-sulfonic Acid Dipropylamide The suspension of 2,3-dihydroxynaphthalene-6-sulphonic acid sodium salt (2.6 g), acetic acid (20 ml), acetic anhydride (10 ml) and sulphuric acid (0.6 ml) was refluxed for 30 minutes. Volatiles were removed under reduced pressure and the remaining solids were refluxed in thionyl chloride (20 ml) for 30 minutes. Volatiles were again evaporated and then methylene chloride (30 ml) and dipropylamine (6.8 ml) added and this mixture stirred at room temperature for two hours. The reaction mixture was washed with 1 M hydrochloric acid (70 ml) and the organic phase evaporated. To the remaining solids were added methanol (100 ml) and concentrated hydrochloric acid (20 ml) and this mixture was stirred at room temperature for 22 hours. Diethyl ether (400 ml) was added and the organic phase was washed three times with water. Ether was evaporated. Yield: 1.3 g.

¹H-NMR (DMSO-d$_6$, 400 MHz): 0.81 (t, 6H, J=7 Hz), 1.40–1.52 (m, 4H), 3.03 (t, 4H, J=8 Hz), 7.21 (s, 1H), 7.33 (s, 1H), 7.45 (dd, 1H, J=9 Hz, 2 Hz), 7.75 (d,1H, J=9 Hz), 8.09 (d, 1H, J=2 Hz),), 9.9 (s, 1H), 10.1 (s, 1H).

(b) 6,7-Dihydroxy-5-nitro-naphthalene-2-sulfonic Acid Dipropylamide

Nitric acid in methylene chloride (0.17 ml in 2.0 ml) added to the solution of the product from the previous step (a) (1.26 g) in ethyl acetate (20 ml) at 0–5° C. The reaction mixture was washed with water and evaporated. Column chromatography on silica with toluene-ethyl acetate-acetic acid 23:1:1 as the eluent yielded a crude product (150 mg) from which part was further purified by HPLC (C-18/acetonitrile, 20 mM pH=3, phosphate buffer 41.5:58.5).

¹H-NMR (DMSO-d$_6$, 400 MHz): 0.81 (t, 6H, J=7 Hz), 1.42–1.53 m, 4H), 3.05 (t, 4H, J=8 Hz), 7.60 (s, 1H), 7.62, (d, 1H, J=8 Hz), 7.70 (dd, 1H, j=8 Hz, 2 Hz), 8.34 (d, 1H, J=2 Hz), n. 11.0 (brs, 2H).

EXAMPLE 12

6,7-Dihydroxy-8-nitro-naphthalene-2-sulfonic Acid Dipropylamide

The other isomer separated by HPLC from example 11(b).

¹H-NMR (DMSO-d$_6$, 400 MHz): 0.80 (t, 6H, J=7 Hz), 1.40–1.51 (m, 4H), 3.05 (t, 4H, J=8 Hz), 7.46 (s, 1H), 7.68 (dd, 1H, j=9 Hz, 2 Hz), 7.84 (dd, 1H, J=2 Hz, <1 Hz) 8.00 (d,1H, J=9 Hz), n. 11.0 (br s, 2H).

EXAMPLE 13

2,3-Dihydroxy-naphthalene-1-carbonitrile (a) 2,3-Dimethoxy-naphthalene-1-carbaldehyde n-Butyl lithium in hexane (1.6 N, 31.3 ml) was gradually added to a solution of 2,3-dimethoxynaphthalene (9.4 g) and N,N,N',N'-tetramethylethylenediamine (7.4 ml) in ether (150 ml) under argon at 0° C. The reaction mixture was stirred at room temperature for two hours, cooled to 0° C. and DMF (7.3 g) in ether (20 ml) added. The reaction mixture was stirred at room temperature overnight and poured in ice water. The product was extracted with ether, washed with water, dried, evaporated and recrystallized from ether. Yield: 4.2 g.

¹H-NMR (DMSO-d$_6$, 400 MHz): 10.68 (s,1H, CHO), 8.95–8.97 (m, 1H), 7.87–7.89 (m,1H), 7.80 (s,1H), 7.49–7.51 (m,2H), 4.00 (s,6H).

(b) 2,3-Dimethoxy-naphthalene-1-carbaldehyde Oxime

The mixture of the product from the previous step (a) (2.0 g), hydroxylamine hydrochloride (0.55 g), water (5 ml), ethanol (6 ml) and sodium hydroxide solution (2.5 N, 3 ml) was refluxed for an hour. Ethanol was evaporated, the solids filtered, washed with water and the crude product recrystallized from ethanol. Yield: 1.25 g, ¹H-NMR (DMSO-d$_6$, 400 MHz): 11.50 (s,1H), 8.73 (d, 1H, J=8 Hz), 8.62 (s,1H), 7.73 (d,1H, J=8 Hz), 7.49 (s,1H), 7.39–7.46 (m,2H), 3.95 (s,3H), 3.83 (s,3H).

(c) 2,3-Dimethoxy-naphthalene-1-carbonitrile

The solution of the product from the previous step (b) (1.2 g) and acetic anhydride (15 ml) was refluxed for 20 minutes. The volatiles were evaporated and the product recrystallized from ethanol. Yield: 0.96 g.

¹H-NMR (DMSO-d$_6$, 400 MHz): 7.94–7.96 (m,1H), 7.88–7.89 (m, 1H), 7.82 (s,1H) 7.55–7.62 (m,3H), 4.06 (s,3H), 3.96 (s,3H).

(d) 2,3-Dihydroxy-naphthalene-1-carbonitrile

Boron tribromide (0.8 ml) was added to the solution of the product from the previous step (c) (0.45 g) in methylene chloride (25 ml) under nitrogen at −20° C. The mixture was stirred at room temperature for two days, poured into ice water, filtered and the product recrystallized from ethanol. Yield: 0.25 g, sublimates.

¹H-NMR (DMSO-d$_6$, 400 MHz): 10.89 (bs, 2H, OH), 7.74–7.76(m, 2H), 7.35–7.47 (m,3H).

EXAMPLE 14

(6,7-Dihydroxy-5-nitro-naphthalen-2-yl)-(4-methyl-piperazin-1-yl)-methanone

Thionyl chloride (0.3 ml) and DMF (one drop) were added to the suspension of the product from example 7(c) (0.35 g) in toluene (10 ml), the mixture was stirred at 80–85° C. for two hours and the volatiles evaporated. The remaining solid was taken in methylene chloride (10 ml), cooled to 0–5° C. and N-methylpiperazine (0,16 ml) in methylene chloride (2 ml) was added gradually. The reaction mixture was stirred for 20 minutes at 0–5° C. and then the product precipitated by adding ether. The resulting solid was suspended in water and neutralized with 1 M NaOH, filtered and washed with water. The crude product was twice recrystallized from ethanol. Yield: 50 mg, melting point over 360° C.

$^1$H-NMR (DMSO-$d_6$, 400 MHz): 7.76 (s,1H), 7.66 (d,1H, J=(8.6 Hz), 7.16 (s,1H), 2.77 (b, 4 H), 2.5 (b, 7 H).

EXAMPLE 15

5-Bromo-6,7-dihydroxy-8-nitro-isoquinolinium; Bromide (a) 6,7-Dimethoxy-8-nitro-isoquinoline To a solution of 6,7-Dimethoxy-isoquinolinone (2.88 g) in sulphuric acid (20 ml) at 5–10° C. was added 2 M $HNO_3$—$H_2SO_4$-solution (8 ml) and the reaction mixture stirred overnight at ambient temperature. The reaction mixture was poured into ice water, pH adjusted to 12 and the product extracted in methylene chloride. The methylene chloride phase was extracted with 1 M HCl, the pH of the aqueous phase adjusted to 12 and extracted into methylene chloride, dried and evaporated. Yield: 2.5 g.

(b) 5-Bromo-6,7-dihydroxy-8-nitro-isoquinolinium; Bromide

The product from the previous step (a) (2.5 g) and 47% hydrobromic acid (50 ml) were refluxed for 12 hours, the reaction mixture evaporated and the product recrystallized from ethanol. Yield: 0.47 g.

$^1$H-NMR (DMSO-$d_6$, 400 MHz): 7.65 (d, 1 H, J=5.6 Hz), 8.05 (d, 1 H, J=5.6 Hz), 9.18 (s, 1H). Mass spectrum: M=284 (100%), 286 (98%), 1 Br.

EXAMPLE 16

1-Nitro-6-phenylazo-naphthalene-2,3-diol

To the suspension of the product from example 1 (0.41 g) in water (10 ml), sodium hydroxide solution (5 M, 0.4 ml) and sodium acetate (0.66 g) were added. The reaction mixture was cooled to 0° C. and benzenediazonium chloride-solution (from 0.18 ml of aniline and 0.14 g $NaNO_2$) was gradually added. After 10 minutes at 0° C. the solution was acidified with 6 M hydrochloric acid, filtered and washed with water. The crude product was triturated with ethanol. Yield: 0.25 g, melting point 238–244° C.

$^1$H-NMR (DMSO-$d_6$): 16.11 (b,1H,OH), 11.5 (b,1H,OH), 8.43 (d,1H, J=8 Hz), 7.85 (d,2H, J=8 Hz), 7.38–7.58 (m,5H), 7.23 (d,1H, J=8 Hz).

EXAMPLE 17

1-(6,7-Dihydroxy-naphthalen-2-ylmethyl)-pyrrole-2,5-dione (a) 6-Chloromethyl-2,3-dimethoxy-naphthalene A solution of the product from preparation example 4(b) (3.14 g) and thionyl chloride (1.6 ml) in methylene chloride (30 ml) was refluxed for three hours. The reaction mixture was evaporated, toluene added and evaporated again. The product was used as such in the following step.

(b) 2-(6,7-Dimethoxy-naphthalen-2-ylmethyl)-isoindole-1,3-dione

To a solution of the product from the previous step (a) in DMF (15 ml) was added potassium phthalimide (2.6 g). After stirring overnight at ambient temperature the reaction mixture was poured in water, extracted into methylene chloride, washed with 1 N sodium hydroxide, dried and evaporated. The resulting mixture was used as such in the following step. (Yield of mixture: 3.3 g).

(c) C-(6,7-Dimethoxy-naphthalen-2-yl)-methylamine

The product mixture from the previous step (b) (3.3 g) and hydrazin hydrate (0.71 ml) in ethanol (100 ml) was refluxed for 8 hours. The reaction mixture was filtered, the filtrate evaporated, triturated with methylene chloride and filtered again. The second filtrate was extracted with 1 M hydrochloric acid, the pH of the aqueous phase taken to 11–12, extracted into methylene chloride again, dried and evaporated. Yield: 0.21 g.

(d) 6-Aminomethyl-naphthalene-2,3-diol; Hydrobromide

The product from the previous step (c) (0.21 g) and 47% hydrobromic acid (10 ml) were refluxed for 5 hours. The reaction mixture was evaporated. Yield: 0.23 g.

(e) 3-[(6,7-Dihydroxy-naphthalen-2-ylmethyl)-carbamoyl]-acrylic acid

To a solution of the product of the previous step (d) (0.23 g) and triethyl amine (0.12 ml) in DMF (3 ml) on ice bath was added maleic anhydride (80 mg). The resulting mixture was stirred at ambient temperature overnight and then poured into ice water. The pH was adjusted to 3 and the product filtered. Yield: 125 mg.

(f) 1-(6,7-Dihydroxy-naphthalen-2-ylmethyl)-pyrrole-2,5-dione

The product from the previous step (e) (125 mg) was refluxed in acetic acid (2 ml) for 20 hours and evaporated. The product was purified by column chromatography on silica with eluent toluene-ethyl acetate-acetic acid 8:9:1. The product was finally triturated with ether. Yield: 18 mg, melting point 182–187° C.

$^1$H-NMR (DMSO-$d_6$, 400 MHz): 4.64 (s, 2H, CH2), 7.03–7.06 (m, 3H), 7.07 (s, 2H, CH=CH), 7.39 (br, 1H), 7.51 (d, J=8,4 Hz), 9.6 (br, 2H, OH).

EXAMPLE 18

1-(6,7-Dihydroxy-5-nitro-naphthalen-2-ylmethyl)-pyrrole-2,5-dione

1-Nitronaphthalene-2,3-diol (0.77 g) produced according to example 1 above and 1-hydroxymethyl-pyrrole-2,5-dione produced according to preparation example 6 below, (0.47 g) were mixed thoroughly and then added in portions to sulphuric acid at 0–5° C. After 30 minutes on ice bath the reaction mixture was poured into ice water and filtered. After chromatography on silica, eluent toluene-ethyl acetate-acetic acid 8:1:1, the product was recrystallized from acetone. Yield: 12 mg, melting point over 350° C.

$^1$H-NMR (DMSO-d$_6$, 400 MHz): 4.69 (s, 2H, CH$_2$), 7.08 (s, 2H, CH=CH), 7.22 (dd, 1H, J=8.4, 1.6 Hz), 7.28 (d, 1H, J=1.6 Hz), 7.32 (s, 1H), 7.73 (d, 1H, J=8.4 Hz), 10.8 (br, 2H, OH).

PREPARATION EXAMPLE 1

6-Benzyl-naphthalene-2,3-diol

Sodium borohydride (0.44 g) was carefully added to a solution of the product from example 3(b) above (0.5 g) in trifluoroacetic acid (20 ml) under nitrogen. The mixture was then stirred at ambient temperature overnight. After treatment with ice water the product was extracted in ether which was dried and evaporated. The crude product was recrystallized from ethanol-water (2:3). Yield: 0.34 g, melting point 177–187° C.

$^1$H-NMR (DMSO-d$_6$): 9.44 (s,1H,OH), 9.40 (s,1H,OH), 7.48 (d,1H, J=8.4 Hz), 7.41 (s,1H), 7.23–7.28 (m,4H), 7.17–7.18 (m,1H), 7.03–7.06 (m,3H), 3.98 (s,2H)

PREPARATION EXAMPLE 2

3-Methoxy-1,6-dinitro-naphthalen-2-ol (a) 3-Methoxy-naphthalen-2-ol

Dimethylsulfate (32 ml) was added to the solution of 2,3-dihydroxynaphthalene (32 g) and sodium hydroxide (10 M, 32 ml) in water (300 ml). After being stirred for six hours at room temperature, the side product 2,3-dimethoxynaphthalene was filtered off (yield 16.6 g). The water phase was acidified, stirred on ice bath, filtered, washed with water and recrystallized from ethanol-water (3:2). Yield: 13.5 g, melting point 108–109° C.

$^1$H-NMR (DMSO-d$_6$): 9.47 (b,1H), 7.69–7.71 (m,1H), 7.60–7.62 (m,1H), 7.22–7.27 (m,3H), 7.14 (s,1H),3.90 (s,3H).

(b) 3-Methoxy-1,6-dinitro-naphthalen-2-ol

Nitric acid in methylene chloride (2 M, 10.0 ml) was added to a solution of the product from the previous step (a) (1.74 g) in methylene chloride (20 ml) at 0° C. The mixture was stirred on ice for an hour and then the precipitated product was filtered. Yield: 1.63 g, melting point 239–242° C.

$^1$H-NMR (DMSO-d$_6$): 11.7–12.4 (b,1H,OH), 9.00 (d,1H, J=2 Hz), 8.28 (dd,1H, J=9 and 2 Hz), 8.07 (s,1H), 7.77 (d,1H, J=9 Hz), 4.13 s,3H).

PREPARATION EXAMPLE 3

4-(6,7-Dihydroxy-naphthalen-2-yl)4-oxo-butyric Acid (a) 4-(6,7-Dimethoxy-naphthalen-2-yl)-4-oxo-butyric Acid Aluminium chloride (9.5 g) was added to a solution of 2,3-dimethoxynaphthalene (10 g) and succinic anhydride 7.1 g in methylene chloride (140 ml). The mixture was stirred at room temperature overnight and then treated with water and filtered. The resulting solid was taken into 1 M sodium hydroxide, washed once with methylene chloride, acidified and filtered. Yield: 8.3 g, melting point 215–229° C.

$^1$H-NMR (DMSO-d$_6$): 12.15 (s,1H,CO$_2$H), 8.53 (s,1H), 7.83 (s,1H), 7.54 (s,1H), 7.39 (s,1H), 3.92 (s,3H), 3.91 (s,3H), 3.33–3.36 (m,2H), 2.60–2.63 (m,2H).

(b) 4-(6,7-Dihydroxy-naphthalen-2-yl)-4-oxo-butyric Acid

The product from the previous step (a) (2 g) and pyridinium hydrochloride (12 g) were heated to 225° C. for 15 minutes. The reaction mixture was allowed to cool to 150–160° C. and then poured into ice. The product was extracted into ethyl acetate and recrystallized from 2-propanol-water. Yield: 0.44 g.

$^1$H-NMR (DMSO-d$_6$, 400 MHz): 12.12 (b,1H,COOH), 9.90 (b,2H,OH), 8.36 (s,1H), 7.70 (dd,1H, J=8 and 1 Hz), 7.65 (d,1H, J=8 Hz), 7.32 (s,1H), 7.18 (s,1H), 331–3.34 (m,2H), 2.59–2.62 (m,2H).

PREPARATION EXAMPLE 4

(6,7-Dimethoxy-naphthalen-2-yl)-methanol (a) 6,7-Dimethoxy-naphthalene-2-carbonyl Chloride DMF (two drops) and thionylchloride (1.9 ml) were added to a suspension of the product from example 7(a) above (3 g) in toluene (50 ml). The reaction mixture was stirred at 80° C. under nitrogen for 200 minutes. The solution was evaporated, toluene added and evaporated again. The product was used as such in the next step.

$^1$H-NMR (CDCl$_3$): 8.59 (d,1H, J=1.7 Hz), 7.96 (dd,1H, J=8.4, 1.7 Hz), 7.76 (d,1H, J=8.4 Hz), 7.27 (s,1H), 7.18 (s,1H), 4.07 (s,3H), 4.05 (s,3H).

(b) (6,7-Dimethoxy-naphthalen-2-yl)-methanol

Lithiumaluminum hydride (1.3 g) was added to a solution of the product from the previous step (a) in THF (50 ml) and the suspension refluxed under nitrogen for 30 minutes. Ethyl acetate (10 ml) was added to the cooled reaction mixture and then the whole suspension was poured into ice water, acidified and extracted into ethyl acetate. The ethyl acetate phase was then washed with water, dried and evaporated. Yield: 3.7 g.

$^1$H-NMR (DMSO-d$_6$, 400 MHz): 7.66–7.73 (m,2H), 7.29–7.32(m,1H), 7.27 (s,2H),5.2 (t,1H, J=5.7 Hz,OH), 4.61 (d,2H, J=5.7 Hz), 3.88 (s,6H).

PREPARATION EXAMPLE 5

4-(6,7-Dihydroxy-naphthalene-2-carbonyl)-1-methyl-piperazin-1-ium; Chloride (a) 6,7-Dihydroxy-naphthalene-2-carbonyl Chloride DMF (two drops) and thionyl chloride (1.6 ml) were added to the suspension of the product from example 7(b) above (1.5 g) in toluene (20 ml). The mixture was stirred at 80° C. for 4 hours, decanted and evaporated. Yield: 1.6 g.

$^1$H-NMR (CDCl$_3$, 400 MHz): 8.79 (s,1H) 8.15 (d,1H, J=8 Hz), 8.00 (d,1H, J=8 Hz), 7.82 (s,1H), 7.72 (s,1H).

(b) 4-(6,7-Dihydroxy-naphthalene-2-carbonyl)-1-methyl-piperazin-1-ium; Chloride

N-Methylpiperazine (0.7 g) in methylene chloride (5 ml) was added to a solution of the product from the previous step (a) (1.5 g) in methylene chloride (15 ml) at 0° C. The reaction mixture was stirred 45 minutes on ice bath, diluted with ether and filtered. Yield: 1.7 g, melting point 176–180° C.

$^1$H-NMR (DMSO-d$_6$, 400 MHz): 11.02 (b,1H), 9.84 (s,1H), 9.77 (s,1H), 7.70 (s 1H),7.64 (d,1H, J=4 Hz), 7.17–7.24 (m, 3H), 3.34–3.41 (m,8H), 2.76 (s, 3H)

PREPARATION EXAMPLE 6

1-Hydroxymethyl-pyrrole-2,5-dione

Maleimide (2.0 g) and 10% formaline (6.8 g) were stirred at 100° C. for 60 minutes. The reaction was let to cool and then kept overnight at 4° C. The product was filtered, washed with water and ethanol. Yield: 1.3 g, melting point 96,5–97° C.

$^1$H-NMR (DMSO-d$_6$, 400 MHz): 7.07 (s,2H), 6.27 (t,1H, J=7 Hz), 4.78 (d,2H, J=7 Hz).

PREPARATION EXAMPLE 7

1-Bromo-naphthalene-2,3-diol (a) 1-Bromo-3-methoxy-naphthalen-2-ol

A solution of bromine (0.26 ml) in methylene chloride (5 ml) was gradually added to the solution of the product from preparation example 2(a) (0.87 g) in methylene chloride (10 ml) at 0° C. The reaction mixture was evaporated and recrystallized from 60% ethanol. Yield: 1.1 g, melting point 100–101° C.

$^1$H-NMR (DMSO-d$_6$): 9.9 (b,1H,OH), 7.93 (d,1H,J=7.9 and 0.9 Hz), 7.32–7.46 (m,1H), 7.40 (s,1H), 7.34–7.38 (m,1H).

(b) 1-Bromo-naphthalene-2,3-diol

Boron tribromide solution in methylene chloride (1 M, 6 ml) was gradually added to a solution of the product from the previous step (a) (0.5 g) in methylene chloride (10 ml) at −10° C. After being stirred two hours below 0° C., the reaction was quenched with ice water and the phases separated. The water phase was extracted with methylene chloride, the combined organic phases washed with water, dried and evaporated. Recrystallization from ethyl acetate-heptane. Yield: 0.32 g, melting point 98–102° C.

$^1$H-NMR (DMSO-d$_6$): 10.51 (s,1H,OH), 9.71 (s,1H,OH), 7.88 (d,1H, J=9 Hz), 7.66 (d,1H, J=8 Hz), 7.27–7.38 (m,2H), 7.18 (s,1H).

PREPARATION EXAMPLE 8

4-Chloro-1-(6,7-dihydroxy-naphthalen-2-yl)-butan-1-one (a) 4-Chloro-1-(6,7-dimethoxy-naphthalen-2-yl)-butan-1-one This product was prepared from 2,3-dimethoxynaphthalene (3.76 g), aluminium chloride (2.93 g) and 4-chlorobutanoylchloride (2.96 g) in methylene chloride (100 ml) as described in example 9(a) above.

$^1$H-NMR (DMSO-d$_6$, 400 MHz): 8.51 (s,1H), 7.83 (s,2H), 7.54 (s,1H), 7.39 (s,1H), 3.93 (s,3H), 3.91 (s,3H), 3.76 (t,2H, J=6.6 Hz), 3.28 (t, 2H, J=7.0 Hz), 2.09–2.16 (m,2H).

(b) 4-Chloro-1-(6,7-dihydroxy-naphthalen-2-yl)-butan-1-one

The product from the previous step (a) (2 g) was reacted with boron tribromide as described in preparation example 7(b). The crude product was triturated with ether. Yield: 0.11 g, melting point 129–135° C.

$^1$H-NMR (DMSO-d$_6$, 400 MHz): 9.90 (b,2H), 8.34 (s,1H), 7.64–7.71 (m,2H), 7.31 (s,1H), 7.12 (s,1H), 3.74 (t,2H, J=8 Hz), 3.24 (t,2H), 2.07–2.14 (m,2H).

PREPARATION EXAMPLE 9

2-Chloro-1-(6,7-dihydroxy-naphthalen-2-yl)-ethanone (a) 2-Chloro-1-(6,7-dimethoxy-naphthalen-2-yl)-ethanone 2,3-Dimethoxynaphthtalene (2.80 g), aluminium chloride (3.33 g) and 3-chloropropionyl chloride (2.79 g) were reacted in methylene chloride (40 ml) as described in example 6(a) above. Yield: 2.87 g, melting point 137–140° C.

$^1$H-NMR (DMSO-d$_6$): 8.54 (s,1H), 7.84 (s,1H), 7.54 (s,1H), 7.40 (s,1H), 3.97–4.00 (m,2H), 3.93 (s,3H), 3.92 (s,3H), 3.63–3.66 (m,2H).

(b) 2-Chloro-1-(6,7-dihydroxy-naphthalen-2-yl)-ethanone

The product from the previous step (a) (1 g) was demethylated with boron tribromide as described in preparation example 7(b) above. Yield: 0.43 g, melting point over 320° C.

$^1$H-NMR (DMSO-d$_6$): 9.5–10.5 (b,2H,OH), 8.38 (s,1H), 7.65–7.72 (m,2H), 7.33 (s,1H), 7.18 (s,1H), 3.95–3.98 (m,2H), 3.60–3.63 (m,2H).

PREPARATION EXAMPLE 10

6,7-Dimethoxy-naphthalene-2-carbaldehyde 2,3-Dichloro-5,6-dicyanobenzoquinone (DDQ) (1.14 g) was gradually added to the solution of the product from preparation example 4(b) above (1.09 g) in dioxane (25 ml) and the reaction mixture stirred at room temperature overnight. The precipitated DDQ-H$_2$ was filtered and the filtrate evaporated. The resulting solids were triturated with methylene chloride and filtered. The filtrate was evaporated and recrystallized from ethanol. Yield: 0.61 g, melting point 87–88° C.

$^1$H-NMR (DMSO-d$_6$, 400 MHz): 10.07 (s,1H,CHO), 8.37 (s,1H), 7.89 (d,1H, J=8 Hz), 7.74 (d,1H, J=8 Hz), 7.54 (s,1H), 7.44 (s,1H), 3.94 (s,3H), 3.93 (s,3H).

PREPARATION EXAMPLE 11

Acetic Acid 6,7-dimethoxy-naphthalen-2-ylmethyl Ester

Acetyl chloride (0.32 ml) was added to the solution of the product from preparation example 4(b) above (1.0 g) and triethyl amine (0.63 ml) in methylene chloride (20 ml) at 0° C. The reaction mixture was allowed to reach room temperature and then it was washed with water, the organic phase dried and evaporated. Yield: 1.2 g, melting point 71–75° C.

$^1$H-NMR (DMSO-d$_6$, 400 MHz): 7.72–7.75 (m,2H), 7.29–7.31 (m,3H), 5.18 (s,2H), 3.88 (s,6H), 2.09 (s,3H).

What is claimed is:

1. A compound of formula I,:

I wherein the two OH— substituents in the phenyl moiety are in a position ortho to one another and R$_1$ is in a position ortho to one of the hydroxy groups;

and wherein

"A" is a fused ring moiety selected from a benzo ring and a 6-membered heteroaromatic ring which contains one or two N heteroatoms;

t is 1,2,3 or 4;

R$_1$ is NO$_2$, CN, CHO or CF$_3$; and each $R_2$ is selected independently from OH, halogen, $NO_2$, SH, $NH_2$, $(C_1-C_6)$alkyl, $(C_2-C_6)$alkenyl, $(C_1-C_6)$alkoxy, OH—$(C_1-C_6)$alkyl, $NH_2$—$(C_1-C_6)$alkyl, halo-$(C_1-C_6)$alkyl, mono- or di$(C_1-C_6)$alkylamino, $SO_2R_4$, $(C_1-C_{20})$alkyl-CO—, halo-$(C_1-C_6)$alkyl, -CO—, phenyl-N═N— optionally substituted with one to three substituents $R_6$, —$(Y)_n$—$(Y)_n$—$(B)_m$—$R_5$;

$R_3$ is H, $NO_2$, CN, CHO, halogen, $CF_3$ or $CH_3$; and $R_4$ is $(C_1-C_6)$alkyl, $NH_2$, OH or mono- or di$(C_1-C_6)$alkylamino;

m is 0 or 1;

n is 1;

Y is —CO— or —CHOH—;

B is $(C_1-C_6)$alkylene or $(C_2-C_6)$alkenylene;

$R_5$ is phenyl, naphthyl, $(C_3-C_7)$cycloalkyl or 5- to 10-membered heterocyclyl with one to four heteroatoms each selected independently from N, O and S, wherein the said phenyl, naphthyl, $(C_3-C_7)$cycloalkyl or 5- to 10-membered heterocyclyl is optionally substituted with one to five substituents $R_6$ or $R_5$ is

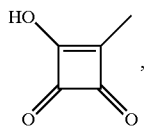

each $R_6$ is selected independently from OH, halogen, COOH, 5-tetrazolyl, $NO_2$, SH, $NH_2$, CN, CHO, ═O, $(C_1-C_6)$alkyl, $(C_1-C_6)$alkoxy, halo-$(C_1-C_6)$alkyl, mono- or di$(C_1-C_6)$alkylamino, CO—$(C_1-C_6)$alkyl, CO—$NH_2$, mono- or di$(C_1-C_6)$alkylamino-CO—, NHOH, CONHOH and $SO_2R_4$;

or a pharmaceutically acceptable salt or pharmaceutically acceptable ester or pharmaceutically acceptable amide thereof.

2. A compound of claim 1, which is a compound of formula Ia:

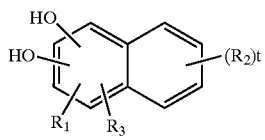

wherein the two OH— substituents are in a position ortho to one another and $R_1$ is in a position ortho to one of the hydroxy groups; and $R_1$ to $R_3$ and t are as defined in claim 1, or a pharmaceutically acceptable salt or pharmaceutically acceptable ester or pharmaceutically acceptable amide thereof.

3. A compound of claim 1, which is a compound of formula Iaa:

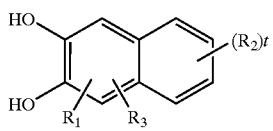

wherein $R_1$ to $R_3$ and t are as defined in claim 1, or a pharmaceutically acceptable salt or pharmaceutically acceptable ester or pharmaceutically acceptable amide thereof.

4. A compound of claim 1, which is a compound of formula Ib or Ic:

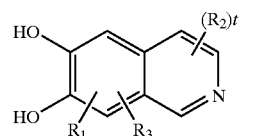

or

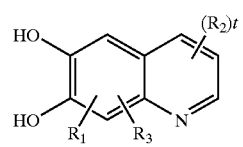

wherein $R_1$ to $R_3$ and t are as defined in claim 1, or a pharmaceutically acceptable salt or pharmaceutically acceptable ester or pharmaceutically acceptable amide thereof.

5. A compound according to claim 1, wherein $R_1$ is $NO_2$, CHO or CN.

6. A compound according to claim 5, wherein $R_1$ is $NO_2$.

7. A compound according to claim 1, wherein $R_3$ is H.

8. A compound according to claim 1, wherein t is 1 or 2 and each $R_2$ is selected independently from OH, $NH_2$, halogen, $NO_2$, $SO_2R_4$, $(C_1-C_6)$alkyl, $NH_2$—$(C_1-C_6)$alkyl, $(C_1-C_{20})$alkyl-CO—, halo-$(C_1-C_6)$alkyl-CO—, phenyl-N═N—, wherein phenyl is optionally substituted with one to three substituent(s) $R_6$, —$(Y)_n$—$(B)_m$—COOH and —$(Y)_n$—$(B)_m$—$R_5$.

9. A compound according to claim 1, wherein $R_2$ is phenyl-N═N, wherein phenyl is optionally substituted with one or two substituent(s) $R_6$, —$(Y)_n$—$(B)_m$—COOH or —$(Y)_n$—$(B)_m$—$R_5$, wherein n is 1 and Y is CO; m is 0 or 1 and B is $(C_1-C_6)$alkylene.

10. A compound according to claim 1, wherein $R_5$ is phenyl optionally substituted with one or two substituent(s) $R_6$ selected independently from OH, halogen, $(C_1-C_6)$alkyl, $(C_1-C_6)$alkoxy, COOH and tetrazolyl; or $R_5$ is tetrazol-5-yl, piperidin-1-yl, piperazin-1-yl, pyrrol-1-yl, pyrrolin-1-yl or pyrrolidin-1-yl, each optionally substituted with one or two substituent(s) $R_6$ selected independently from $(C_1-C_6)$alkyl, $(C_1-C_6)$alkoxy and ═O.

11. A compound according to claim 10, wherein $R_5$ is phenyl optionally substituted with one or two $R_6$, or $R_5$ is tetrazol-5-yl, 4-$(C_1-C_6)$alkyl-piperazin-1-yl or pyrrole-2,5-dion-1-yl.

12. A compound according to claim 10, wherein $R_5$ is tetrazol-5-yl or phenyl which is optionally substituted with one or two COOH or tetrazolyl.

13. A pharmaceutical composition which comprises as an active agent a compound of formula I':

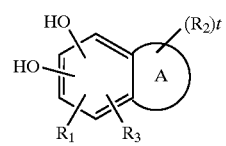

wherein the two OH— substituents in the phenyl moiety are in a position ortho to one another and $R_1$ is in a position ortho to one of the hydroxy groups; and wherein "A" is a fused ring moiety selected from a benzo ring and a 6-membered heteroaromatic ring which contains one or two N heteroatoms;

$R_1$ is $NO_2$, CN, CHO, $CF_3$ or $(C_1-C_6)$alkyl-CO—;

t is 0, 1,2,3 or 4;

each $R_2$ is selected independently from OH, halogen, $NO_2$, SH, $NH_2$, $(C_1-C_6)$alkyl, $(C_2C_5)$alkenyl, $(C_1-C_6)$alkoxy, OH—$(C_1-C_6)$alkyl, $NH_2$—$(C_1-C_6)$alkyl, halo-$(C_1-C_6)$alkyl, mono- or di$(C_1-C_6)$alkylamino, $SO_2R_4$, $(C_1-C_{20})$alkyl-CO—, halo-$(C_1-C_6)$alkyl-CO—, phenyl-N=N— optionaliy substituted with one to three substituents $R_6$, —$(Y)_n$—$(B)_m$—COOH and —$(Y)_n$—$(B)_m$—$R_5$;

$R_3$ is H, $NO_2$, CN, CHO, halogen, $CF_3$ or $(C_1-C_6)$alkyl; and $R_4$ is $(C_1-C_6)$alkyl, $NH_2$, OH or mono- or di$(C_1-C_6)$alkylamino;

m is 0 or 1;

n is 1;

Y is —CO— or —CHOH—;

B is $(C_1-C_6)$alkylene or $(C_2-C_6)$alkenylene;

$R_5$ is phenyl, naphthyl, $(C_3-C_7)$cycloalkyl or 5- to 10-membered heterocyclyl with one to four heteroatoms each selected independently from N, O and S, wherein the said phenyl, naphthyl, $(C_3-C_7)$cycloalkyl or 5- to 10-membered heterocyclyl is optionally substituted with one to five substituents $R_6$;

or $R_5$ is

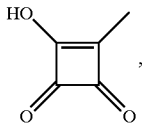

each $R_6$ is selected independently from OH, halogen, COOH, 5-tetrazolyl, $NO_2$, SH, $NH_2$, CN, CHO, =O, $(C_1-C_6)$alkyl, $(C_1-C_6)$alkoxy, halo-$(C_1-C_6)$alkyl, mono- or di$(C_1-C_6)$alkylamino, CO—$(C_1-C_6)$alkyl, CO—$NH_2$, mono- or di$(C_1-C_6)$alkylamino-CO—, NHOH, CONHOH and $SO_2R_4$;

or a pharmaceutically acceptable salt or pharmaceutically acceptable ester or pharmaceutically acceptable amide thereof, and a pharmaceutically acceptable excipient.

14. A method for treating Parkinson's Disease, which comprises administering to a mammal in need of the treatment an effective amount of levodopa and an effective amount of the compound of formula I':

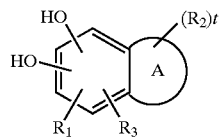

wherein the two OH— substituents in the phenyl moiety are in a position ortho to one another and $R_1$ is in a position ortho to one of the hydroxy groups; and wherein "A" is a fused ring moiety selected from a benzo ring and a 6-membered heteroaromatic ring which contains one or two N heteroatoms;

$R_1$ is $NO_2$, CN, CHO, $CF_3$ or $(C_1-C_6)$alkyl-CO—;

t is 0, 1,2,3 or 4;

each $R_2$ is selected independently from OH, halogen, $NO_2$, SH, $NH_2$, $(C_1-C_6)$alkyl, $(C_2-C_6)$alkenyl, $(C_1-C_6)$alkoxy, OH—$(C_1-C_6)$alkyl, $NH_2$—$(C_1-C_6)$alkyl, halo-$(C_1-C_6)$alkyl, mono- or di$(C_1-C_6)$alkylamino, $SO_2R_4$, $(C_1-C_{20})$alkyl-CO—, halo-$(C_1-C_6)$alkyl-CO—, phenyl-N=N- optionally substituted with one to three substituents $R_6$,—$(Y)_n$—$(B)_m$—COOH and —$(Y)_n$—$(B)_m$—$R_5$;

$R_3$ is H, $NO_2$, ON, CHO, halogen, $CF_3$ or $(C_1-C_6)$alkyl; and $R_4$ is $(C_1-C_6)$alkyl, $NH_2$, OH or mono- or di$(C_1-C_6)$alkylamino;

m is 0 or 1;

n is 1;

Y is —CO— or —CHOH—;

B is $(C_1-C_6)$alkylene or $(C_2-C_6)$alkenylene;

$R_5$ is phenyl, naphthyl, $(C_3-C_7)$cycloalkyl or 5- to 10-membered heterocyclyl with one to four heteroatoms each selected independently from N, O and S, wherein the said phenyl, naphthyl, $(C_3-C_7)$cycloalkyl or 5- to 10-membered heterocyclyl is optionally substituted with one to five substituents $R_6$ or $R_5$ is

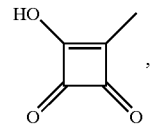

each $R_6$ is selected independently from OH, halogen, COOH, 5-tetrazolyl, $NO_2$, SH, $NH_2$, CN, CHO, =O, $(C_1-C_6)$alkyl, $(C_1-C_6)$alkoxy, halo-$(C_1-C_6)$alkyl, mono- or di$(C_1-C_6)$alkylamino, CO—$(C_1-C_6)$alkyl, CO—$NH_2$, mono- or di$(C_1-C_6)$alkylamino-CO—, NHOH, CONHOH and $SO_2R_4$;

or pharmaceutically acceptable salt or pharmaceutically acceptable ester or pharmaceutically acceptable amide thereof to potentiate the levodopa therapy.

15. A method for treating Parkinson's Disease, which comprises administering to a mammal in need of the treatment an effective amount of levodopa and an effective amount of a compound according to claim 1 to potentiate levodopa therapy.

16. A pharmaceutical composition which comprises as an active agent a compound according to claim 1 and a pharmaceutically acceptable excipient.

* * * * *

UNITED STATES PATENT AND TRADEMARK OFFICE
CERTIFICATE OF CORRECTION

PATENT NO. : 6,903,114 B2
DATED : June 7, 2005
INVENTOR(S) : Reijo Bäckström et al.

It is certified that error appears in the above-identified patent and that said Letters Patent is hereby corrected as shown below:

Column 27,
Line 5, "halo-$(C_1-C_6)$alkyl, -CO-" should read -- halo-$(C_1-C_6)$alkyl-CO- --.
Line 7, "$R_6$, $-(Y)_n$ $-(Y)_n$ $-(B)_m$ $-R_5$;" should read -- $R_6$, $-(Y)_n$-$(B)_m$-COOH and $-(Y)_n$ $-(B)_m$ $-R_5$; --.

Column 29,
Line 4, "$(C_2-C_5)$ alkenyl" should read -- $(C_2-C_6)$ alkenyl --.
Line 8, "optionaliy" should read -- optionally --.

Column 30,
Line 16, "ON" should read -- CN --.
Line 41, insert a space before "SH".

Signed and Sealed this

Thirtieth Day of August, 2005

JON W. DUDAS
*Director of the United States Patent and Trademark Office*